(12) United States Patent
Hotter et al.

(10) Patent No.: US 9,499,504 B2
(45) Date of Patent: Nov. 22, 2016

(54) CRYSTALLINE FORM OF VORTIOXETINE HYDROBROMIDE

(71) Applicant: Sandoz AG, Basel (CH)

(72) Inventors: Andreas Hotter, Kundl (AT); Michael Enders, Innsbruck (AT); Ulrich Griesser, Axamas (AT)

(73) Assignee: Sandoz AG (CH)

( * ) Notice: Subject to any disclaimer, the term of this patent is extended or adjusted under 35 U.S.C. 154(b) by 0 days.

(21) Appl. No.: 14/429,388

(22) PCT Filed: Sep. 18, 2013

(86) PCT No.: PCT/EP2013/069401
§ 371 (c)(1),
(2) Date: Mar. 19, 2015

(87) PCT Pub. No.: WO2014/044721
PCT Pub. Date: Mar. 27, 2014

(65) Prior Publication Data
US 2015/0266841 A1     Sep. 24, 2015

(30) Foreign Application Priority Data
Sep. 19, 2012   (EP) .................................... 12185103

(51) Int. Cl.
*C07D 295/096*     (2006.01)
*A61K 31/495*      (2006.01)

(52) U.S. Cl.
CPC ......... *C07D 295/096* (2013.01); *A61K 31/495* (2013.01)

(58) Field of Classification Search
None
See application file for complete search history.

(56) References Cited

FOREIGN PATENT DOCUMENTS

| | | |
|---|---|---|
| CN | 101636161 A | 1/2010 |
| CN | 102405048 A | 4/2012 |
| WO | 03029232 A1 | 4/2003 |
| WO | 2007144005 A1 | 12/2007 |
| WO | 2008113359 A2 | 9/2008 |
| WO | 2010094285 A1 | 8/2010 |
| WO | 2010121621 A1 | 10/2010 |

OTHER PUBLICATIONS

International Search Report and Written Opinion, PCT/EP2013/069401, date of mailing Oct. 15, 2013, 9 pages.
Brittain et al., Methods for the Characterization of Polymorphs, Polymorphism in Pharmaceutical Solids, Jan. 1, 1999, pp. 235-238.
Brittain, Harry G., X-ray Diffraction III: Pharmaceutical Applications of X-ray Powder Diffraction, Pharmaceutical Technology, Mar. 2001, pp. 142-150.
Official action issued by Chinese Patent Office, Date of official communication: Apr. 18, 2016, For Chinese Patent Application No. 201380060097.9.
English Translation of Official action issued by Chinese Patent Office, Date of official communication: Apr. 18, 2016, For Chinese Patent Application No. 201380060097.9.

*Primary Examiner* — Emily Bernhardt
(74) *Attorney, Agent, or Firm* — Luedeka Neely Group, P.C.

(57) ABSTRACT

The present invention is directed to a crystalline compound comprising a hydrobromide acid (HBr) salt of a compound of formula (I) (1-{2-[(2,4-dimethylphenyl)sulfanyl]phenyl}piperazine, INN: vortioxetine), having an XRPD pattern with characteristic peaks (expressed in 2θ±0.2° 2θ (CuKα radiation)) at 5.5°, 14.8°, 16.7° and 20.0° and processes for obtaining the same.

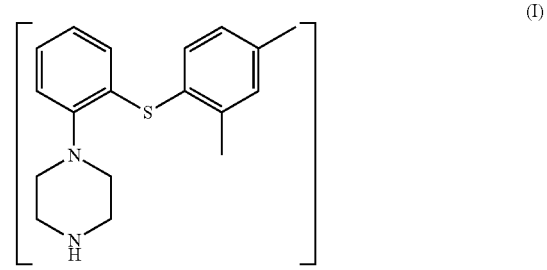

(I)

13 Claims, 12 Drawing Sheets

CRYSTALLINE FORM OF VORTIOXETINE HYDROBROMIDE

This application is a national phase entry of PCT International application number PCT/EP2013/069401, filed Sep. 18, 2013. This application also claims the benefit of the earlier filing date of EP 12185103.4, filed Sep. 19, 2012.

FIELD OF THE INVENTION

The present invention relates to a novel polymorph and a novel hydrate of vortioxetine hydrobromide as well as to the preparation thereof. The novel hydrate is a valuable intermediate for the preparation of the novel polymorph of vortioxetine hydrobromide. Moreover the present invention relates to the use of the novel polymorph for the preparation of a medicament. In addition the present invention relates to pharmaceutical compositions comprising an effective amount of the novel polymorph of vortioxetine hydrobromide and to methods of preparing the same.

BACKGROUND OF THE INVENTION

1-{2-[(2,4-dimethylphenyl)sulfanyl]phenyl}piperazine hydrobromide, also known as vortioxetine hydrobromide, is a multimodal serotonergic compound currently in clinical development for major depressive disorder and generalized anxiety disorder. It has been disclosed in the art that the compound shows antagonistic properties at $5\text{-}HT_{3A}$ and $5\text{-}HT_7$, receptors, partial agonistic properties at $5\text{-}HT_{1B}$ receptors, agonistic properties at $5\text{-}HT_{1A}$ receptors and potent serotonin reuptake inhibition via inhibition of the serotonin transporter (SERT). Vortioxetine hydrobromide is represented by the following general formula A:

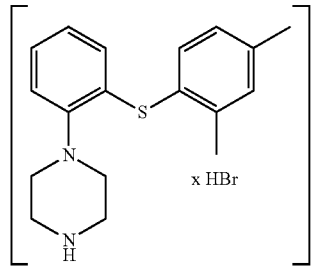

General formula A

WO 2003/029232 A1 discloses vortioxetine and pharmaceutically acceptable salts thereof per se as well as pharmaceutical compositions comprising the same. However, only a concrete example for preparing vortioxetine free base is given in said application.

WO 2007/144005 A1 discloses crystalline vortioxetine base and a variety of crystalline vortioxetine salts, comprising polymorphs of vortioxetine hydrobromide as well as a hemihydrate and an ethyl acetate solvate thereof, and crystalline vortioxetine hydrochloride and a monohydrate thereof. Crystalline vortioxetine mesylate, hydrogenfumarate, hydrogenmaleate, mesohydrogentartrate, L-(+)-hydrogentartrate, D-(−)-hydrogentartrate, hydrogen sulphate, dihydrogenphosphate and nitrate are also disclosed.

WO 2010/094285 A1 discloses an isopropanol solvate of vortioxetine hydrobromide as well as a process for the purification of vortioxetine and pharmaceutically acceptable salts thereof.

Polymorphism is a phenomenon relating to the occurrence of different crystalline forms for one molecule. There may be several different crystalline forms for the same molecule with distinct crystal structures and varying in physical properties like melting point, XRPD pattern and FTIR spectrum. These polymorphs are thus distinct solid forms which share the molecular formula of the compound from which the crystals are made up, however they may have distinct advantageous physical properties such as e.g. chemical stability, physical stability, hygroscopicity, solubility, dissolution rate, morphology or bioavailability. In addition the preparation process of a crystalline form plays an important role in the development of an active pharmaceutical ingredient. It is essential that the crystallization process is robust and reliably produces the desired crystalline form in polymorphically pure form.

The acceptable amount of solvents in an active pharmaceutical ingredient is strictly regulated e.g. by the ICH guideline for residual solvents. Solvates of vortioxetine hydrobromide such as e.g. the ethyl acetate solvate of WO 2007/144005 A1 and the isopropanol solvate of WO 2010/094285 A1 are no suitable crystalline forms for the preparation of a medicament as they clearly exceed the recommended solvent amount for class 3 solvents. In summary, solvates of vortioxetine hydrobromide know in the art are no suitable forms for the preparation of a medicament due to the strict limits for residual solvents in an active pharmaceutical ingredient.

In addition, an active pharmaceutical ingredient is preferably non-hygroscopic in order to ensure the chemical and physical quality during the storage of the active substance itself and during the shelf-life of a solid finished dosage form containing the active substance without the need of special and expensive packaging. However, according to the presented data in WO 2007/144005 A1 the gamma form and the hemihydrate of vortioxetine hydrobromide disclosed in WO 2007/144005 A1 significantly take up water at increased relative humidities and are therefore not favored for the preparation of a solid medicament.

Furthermore the bioavailability of a compound intended to be administered orally, is dependent on the compounds solubility as well as the compounds permeability according to the biopharmaceutical classification system (BCS). Therefore a drug substance having high solubility which is consequently highly bioavailable is desired.

Finally the crystalline forms alpha, beta and the ethyl acetate solvate of WO 2007/144005 A1 as well as the crystalline form gamma and the hemihydrate of WO 2007/144005 A1 are difficult to make in a reliable manner because these forms are obtained via crystallizations from the same solvent systems. As the ethyl acetate solvate and the polymorphs alpha and beta are all obtained via crystallizations from ethyl acetate and the form gamma and the hemihydrate are both obtained via crystallizations from water the production processes are especially critical and sensitive because the single crystalline forms are only obtained in pure form in a quite narrow range of critical parameters, such as the crystallization temperature, the concentration and the stirring time as described in the concrete examples 4a, 4c, 4e, 4g and 4i of WO 2007/144005 A1.

The technical problem underlying the present invention is to circumvent the drawbacks of the known crystalline forms of vortioxetine hydrobromide disclosed in the state of the art such as toxicity issues of solvates, stability issues due to water uptake, bioavailability issues due to limited solubility and preparation issues due to similar crystallization processes by providing a non-solvated crystalline form of vortioxetine hydrobromide which is non-hygroscopic, shows high solubility and is obtained in polymorphically pure form in an easy and reliable manner.

SUMMARY OF THE INVENTION

The technical problem underlying the present invention is solved by a crystalline compound comprising a hydrobromic acid (H Br) salt of a compound of formula I (1-{2-[(2,4-dimethylphenyl)sulfanyl]phenyl}piperazine, INN: vortioxetine), formula I

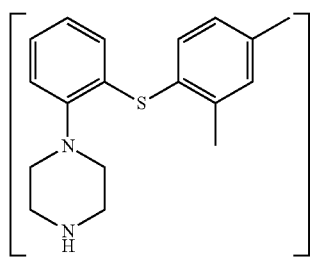

having an XRPD pattern with characteristic peaks (expressed in 2θ±0.2° 2θ (CuKα radiation)) at 5.5°, 14.8°, 16.7° and 20.0°.

Preferably, the crystalline compound has an XRPD pattern with characteristic peaks (expressed in 2θ±0.2° 2θ (CuKα radiation)) at 5.5°, 14.8°, 16.7°, 20.0°, 27.6°, 28.1°, 28.4°, 28.6°, 29.1°, 30.5° and 34.4°.

The crystalline compound of the present invention is an anhydrous and non-solvated crystalline form and shows unexpected advantages compared to the known forms alpha, beta, gamma, the hemihydrate and the ethyl acetate solvate of vortioxetine hydrobromide of WO 2007/144005 A1 and also compared to the isopropanol solvate of WO 2010/094285 A1, making the crystalline compound of the present invention especially suitable for the preparation of a solid medicament.

Preferably, the molar ratio of the compound of formula I and the hydrobromic acid in the crystalline compound is in the range of from 1:0.8 to 1:1.2, even more preferred 1:0.9 to 1:1.1 and most preferred approximately 1:1.

In a further preferred embodiment, the crystalline compound has an infrared spectrum comprising peaks at wavenumbers of 2484±2 cm$^{-1}$, 2472±2 cm$^{-1}$, 1586±2 cm$^{-1}$, 1438±2 cm$^{-1}$ and 764±2 cm$^{-1}$.

Preferably, the crystalline compound has a water content of less than 0.7 wt-%.

In a further preferred embodiment, the crystalline compound has an amount of residual solvents of less than 0.2 wt-%.

In a further preferred embodiment, the crystalline compound has an average particle size ranging from about 1 to about 100 μm.

In a further preferred embodiment the present invention relates to a process for preparing the crystalline compound of the present invention. Preferably, a novel hydrate of vortioxetine hydrobromide is employed as an intermediate.

The novel crystalline hydrate of vortioxetine hydrobromide is exhibiting monoclinic cells having space group P2$_1$/c. and having the parameters a=37.33+/−0.6 Å
b=6.46+/−0.1 Å
c=31.36+/−0.5 Å
α=90°
β=94.9°+/−0.5°
γ=90°
Z=16 as determined by X-ray structural analysis. Preferably, the molar ratio of vortioxetine hydrobromide and water is in the range from 1:0.8 to 1:1.2, preferably from 1:0.9 to 1.1 and most preferred approximately 1:1. In a preferred embodiment, the crystalline hydrate of vortioxetine hydrobromide is vortioxetine hydrobromide monohydrate.

In the method for the preparation of the crystalline compound of the present invention vortioxetine hydrobromide hydrate is heated to a temperature ranging from 120° C. to 150° C., preferably ranging from 120° C. to 140° C. and recovering the crystals. In a preferred embodiment, the above described hydrate of vortioxetine hydrobromide of the present invention is heated to a temperature ranging from 120° C. to 150° C., preferably ranging from 120° C. to 140° C. and recovering the crystals.

A preferred aspect of the present invention is a method for the preparation of the crystalline hydrate of vortioxetine hydrobromide of the present invention comprising the step of evaporating an aqueous alcoholic solution of vortioxetine hydrobromide at room temperature and recovering the crystals, wherein the alcohol comprised in the alcoholic solution is preferably selected from methanol, ethanol or mixtures thereof. The concentration of the alcohol in the aqueous alcoholic solution may be in the range from 50 to 96 wt-%, more preferably from 50 to 80 wt-% and most preferably from 50 to 65 wt-%.

Preferably, the process of obtaining the novel hydrate of vortioxetine hydrobromide comprises the steps of evaporating an aqueous ethanolic or methanolic solution of vortioxetine hydrobromide at room temperature and recovering the crystals.

The crystalline hydrate of vortioxetine hydrobromide of the present invention can be used as an intermediate for the production of the crystalline compound of the present invention.

A further aspect of the present invention is directed to a pharmaceutical composition comprising the crystalline compound of the present invention and at least one pharmaceutically acceptable excipient. The pharmaceutical composition may be an oral dosage form, preferably a tablet and/or capsule.

In addition the present invention relates to the use of the crystalline compound of the present invention for the preparation of a solid medicament.

In another embodiment the present invention relates to solid pharmaceutical compositions comprising an effective amount of the crystalline compound of the present and a pharmaceutically acceptable carrier as well as to processes of preparing the same.

Moreover, the present invention is directed to the pharmaceutical composition of the present invention and/or the crystalline compound of the present invention for use in the treatment of major depressive disorder and/or generalized anxiety disorder.

DETAILED DESCRIPTION OF THE INVENTION

As used herein the term "room temperature" indicates that the applied temperature is not critical and that no exact temperature value has to be kept. Usually, "room temperature" is understood to mean temperatures of about 15° C. to about 25° C. [see e.g. EU Pharmacopoeia 7.5, 1.2(2012)].

The term "solvate" as used herein describes a crystalline compound in which solvent molecules are incorporated into the crystal lattice of the compound in a stoichiometric or non-stoichiometric manner. If the solvent molecules are water the term "hydrate" is used herein. Depending on the molar ratio of water molecules to vortioxetine hydrobromide molecules the term "hemihydrate" (0.3 to 0.7 mol water per mol vortioxetine hydrobromide) or "monohydrate" (0.8 to 1.2 mol water per mol vortioxetine hydrobromide) is used herein.

The term "non-hygroscopic" as used herein indicates that the increase in mass of a drug substance between about 0% to 80% relative humidity is less than 0.2%.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

In a first aspect the present invention relates to a crystalline compound comprising a hydrobromic acid (HBr) salt of vortioxetine, as disclosed above (hereinafter also designated as form "delta").

The term "form alpha" as used herein indicates the solid form of vortioxetine hydrobromide of WO 2007/144005 A1 designated as alpha (see Examples 4a and 4b of WO 2007/144005 A1). The term "form beta" as used herein indicates the solid form of vortioxetine hydrobromide of WO 2007/144005 A1 designated as beta (see Examples 4c and 4d of WO 2007/144005 A1). The term "form gamma" as used herein indicates the solid form of vortioxetine hydrobromide of WO 2007/144005 A1 designated as gamma (see Examples 4e and 4f of WO 2007/144005 A1).

Figure 1:
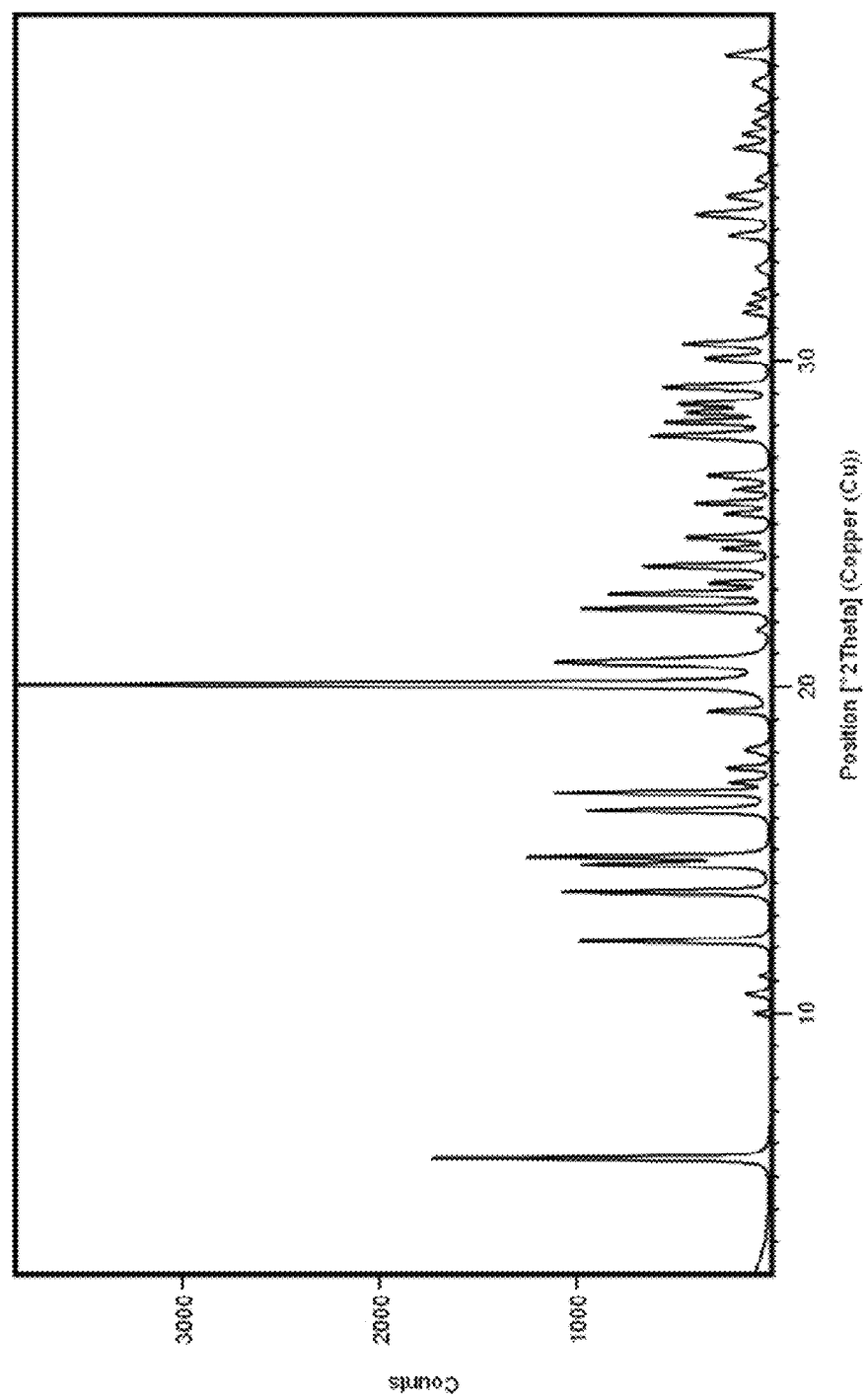
FIG. 1: X-ray powder diffractogram (XRPD) of vortioxetine hydrobromide form delta

The crystalline compound of the present invention can be characterized by showing an X-ray powder diffractogram comprising characteristic peaks (expressed in 2θ±0.2° 2θ (CuKα radiation)) at 5.5°, 14.8°, 16.7° and 20.0°. The X-ray powder diffractogram of the crystalline compound of the present invention comprises additional characteristic peaks at 2-theta angles of 12.2°, 13.7°, 14.5°, 16.2°, 20.7°, 22.4°, 22.8°, 23.7°, 24.6°, 25.6°, 27.6°, 28.1°, 28.4°, 28.6°, 29.1°, 30.5° and 34.4°. A representative diffractogram is displayed in FIG. 1.

Figure 2:
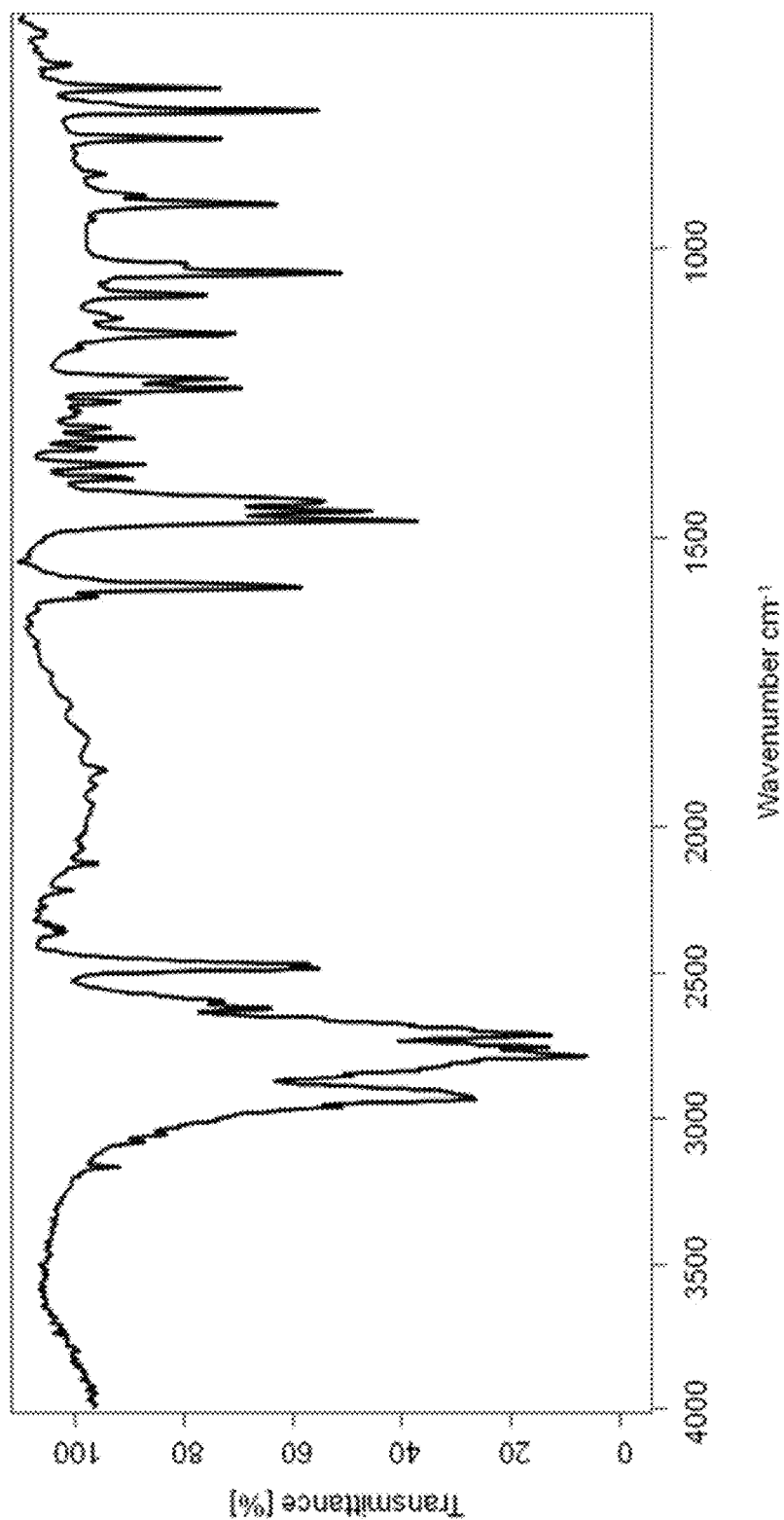
FIG. 2: Fourier transform infrared (FTIR) spectrum of vortioxetine hydrobromide form delta

In addition the crystalline compound of the present invention can be characterized by showing an FTIR-spectrum comprising peaks at wavenumbers of 2484±2 cm$^{-1}$, 2472±2 cm$^{-1}$, 1586±2 cm$^{-1}$, 1438±2 cm$^{-1}$ and 764±2 cm$^{-1}$. The FTIR-spectrum of the crystalline compound of the present invention comprises additional characteristic peaks at wavenumbers of 3166±2$^{-1}$, 2959±2 cm$^{-1}$, 2931±2 cm$^{-1}$, 2786±2 cm$^{-1}$, 2753±2 cm$^{-1}$, 2713±2 cm$^{-1}$, 2621±2 cm$^{-1}$, 2596±2 cm$^{-1}$, 1601±2 cm$^{-1}$, 1471±2 cm$^{-1}$, 1454±2 cm$^{-1}$, 1398±2 cm$^{-1}$, 1375±2 cm$^{-1}$, 1346±2 cm$^{-1}$, 1329±2 cm$^{-1}$, 1312±2 cm$^{-1}$, 1267±2 cm$^{-1}$, 1243±2 cm$^{-1}$, 1227±2 cm$^{-1}$, 1149±2 cm$^{-1}$, 112±2 cm$^{-1}$, 1081±2 cm$^{-1}$, 1043±2 cm$^{-1}$, 925±2 cm$^{-1}$, 910±2 cm$^{-1}$, 873±2 cm$^{-1}$, 813±2 cm$^{-1}$, 725±2 cm$^{-1}$, 685±2 cm$^{-1}$ and 629±2 cm$^{-1}$. A representative FTIR spectrum is displayed in FIG. 2.

Figure 3:
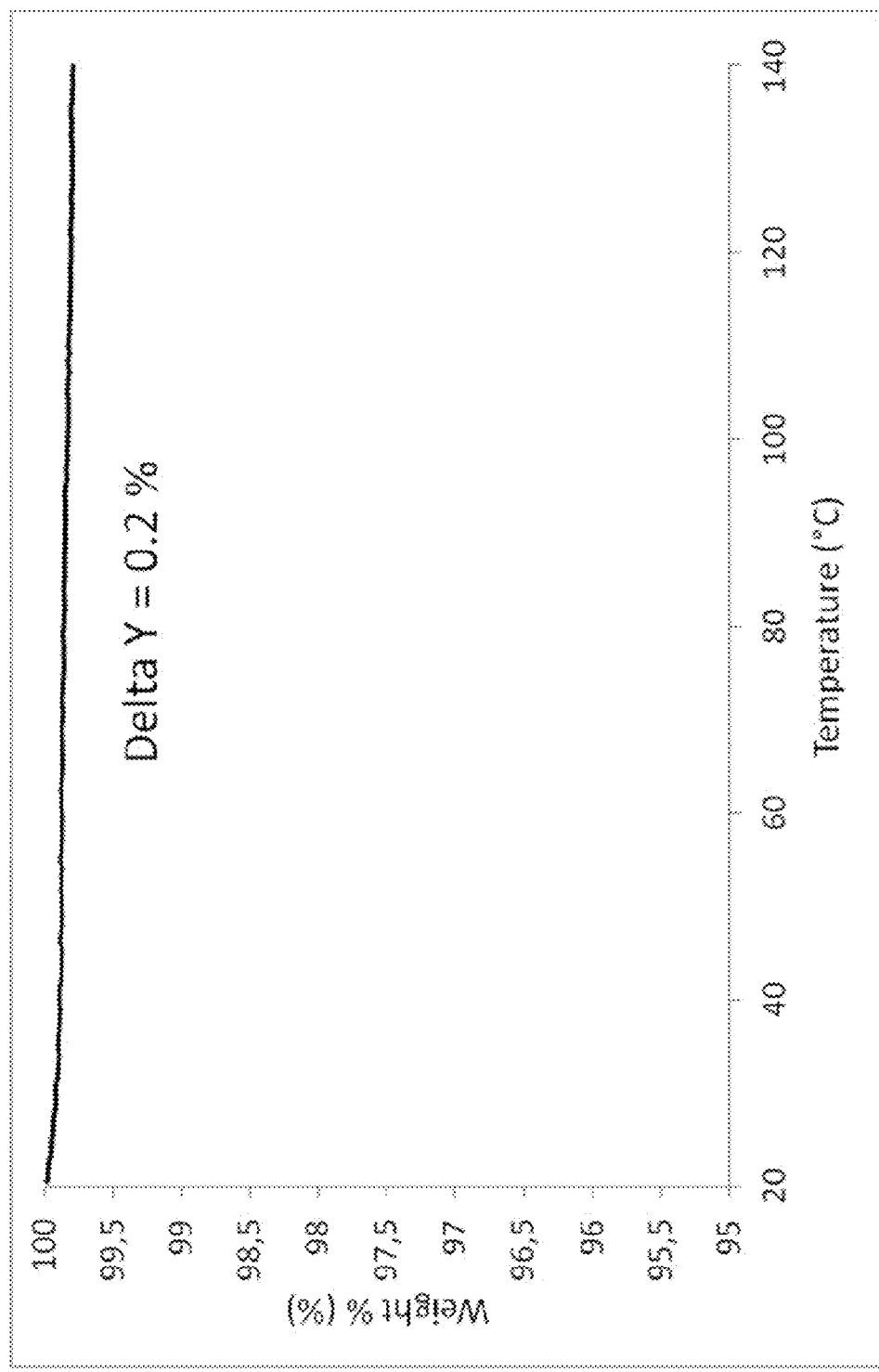
FIG. 3: Thermogravimetric analyses (TGA) curve of the crystalline compound of the present invention

Furthermore the crystalline compound of the present invention can be characterized as being a non-solvated form containing less than about 0.5% of an organic solvent as determined by thermogravimetric analysis. The representative TGA curve displayed in FIG. 3 shows a mass loss of about 0.2% until 140° C.

Figure 4:
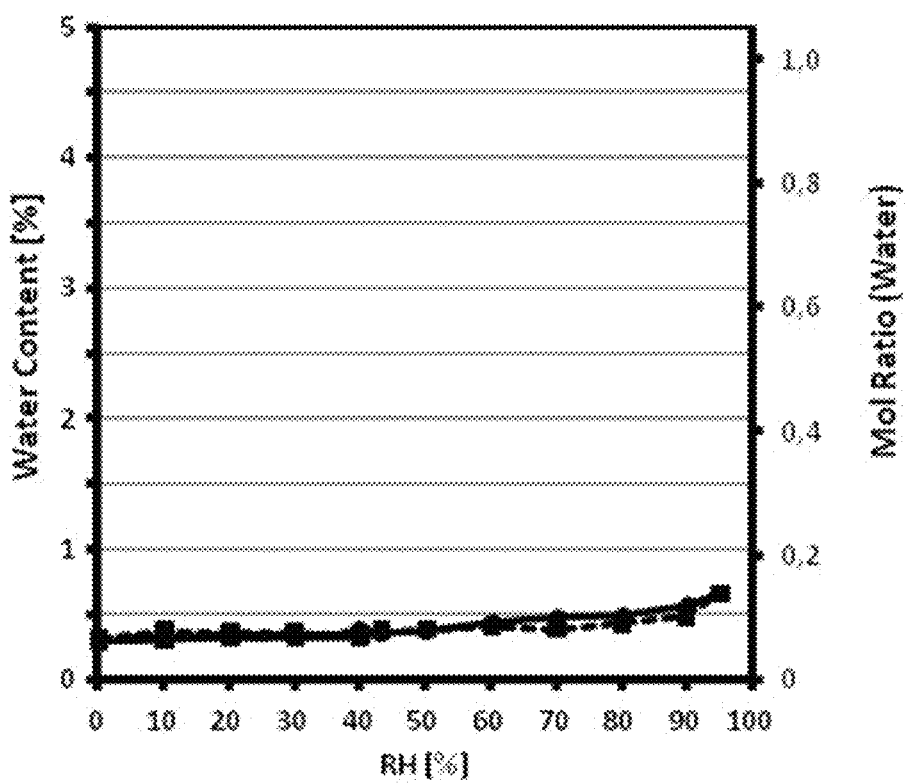
FIG. 4: Gravimetric moisture sorption/desorption cycle of vortioxetine hydrobromide form delta

Finally, the crystalline compound of the present invention can be characterized as being an anhydrous form. E.g. it contains less than about 0.7% water up to a relative humidity of about 95%. A representative gravimetric moisture sorption/desorption cycle is displayed in FIG. 4.

The present invention also relates to a process for the preparation of the crystalline compound of the present invention comprising heating the novel hydrate of vortioxetine hydrobromide of the present invention and recovering polymorph delta.

Typically the novel hydrate of vortioxetine hydrobromide of the present invention is heated to a temperature ranging from about 120 to 150° C., preferably from about 120 to 140° C. for a certain period of time. Typically, depending on the applied temperature, several minutes to several hours are required to complete the transformation, e.g. at a temperature of about 120° C. the transformation is complete in less than 8 hours. The transformation may be monitored by classical methods such as XRPD.

The particle size of the crystalline compound of the present invention obtained according to the process of the present invention typically ranges from about 1 to 100 μm determined by optical light microscopy. However, the particle size can be decreased by any conventional method such as e.g. milling or grinding. In addition the particle size can be homogenized by applying an additional sieving step. Preferably milling and sieving are performed in such a manner that the crystalline compound of the present invention has a particle size ranging from about 0.1 to 50 μm, more preferably from about 0.1 to 25 μm and most preferably from about 0.1 to 15 μm.

The acceptable amount of solvents in an active pharmaceutical ingredient is strictly regulated e.g. by the ICH guideline for residual solvents. Solvates of vortioxetine hydrobromide such as e.g. the ethyl acetate solvate of WO 2007/144005 A1 and the isopropanol solvate of WO 2010/

094285 A1 are no suitable crystalline forms for the preparation of a medicament as they clearly exceed the recommended solvent amount for class 3 solvents (limit 0.5%). For instance, the theoretical amount of ethyl acetate for a monosolvate is about 18.8% and the theoretical amount of isopropanol for a monosolvate is about 13.7%. As can be seen from the TGA curve in FIG. 3 the polymorph of the present invention is a non-solvated form showing a weight loss of about 0.2% until 140° C. and is thus well within the acceptable limits for residual class 3 solvents (such as e.g. ethanol which is used for the preparation of the monohydrate in example 2 of the present invention, which is then dried to form delta). Therefore the novel polymorph delta of the present invention is especially suitable for the preparation of a medicament.

In addition, an active pharmaceutical ingredient is preferably non-hygroscopic in order to ensure the chemical and physical quality during the storage of the active substance itself. Furthermore, an active pharmaceutical ingredient is preferably non-hygroscopic in order to ensure the chemical and physical quality also during the shelf-life of a solid finished dosage form containing the active substance. Special and expensive packaging can then be avoided. However, according to the presented data in examples 4f and 4h of WO 2007/144005 A1, the gamma form and the hemihydrate of vortioxetine hydrobromide disclosed in WO 2007/144005 A1 significantly take up water at increased relative humidities, and are therefore not favored for the preparation of a solid medicament. For instance, in example 4f of WO 2007/144005 A1, it is mentioned that form gamma absorbs about 4.5% water when exposed to high relative humidity and in example 4h of the same application it is stated that the water content of the hemihydrate strongly depends on the relative humidity. For instance, the water content of the hemihydrate at 95% relative humidity is about 3.7% according to example 4h of WO 2007/144005. As can be seen from the gravimetric moisture sorption desorption curve in FIG. 4 the compound of the present invention contains about 0.3% water at a relative humidity of about 0% and about 0.5% water at a relative humidity of about 80% and is therefore non-hygroscopic according to the specifications of the European Pharmacopoeia. Hence the compound of the present invention is especially suitable for the preparation of a solid medicament.

Furthermore the bioavailability of a compound intended to be administered orally is dependent on the compound's solubility as well as the compound's permeability according to the biopharmaceutical classification system (BCS). It is therefore desirable to provide a solid form of a drug substance having high solubility, and which is consequently highly bioavailable.

According to WO 2007/144005 A1, the solubilities of vortioxetine hydrobromide forms alpha and beta in water are 2 mg/mL and 1.2 mg/mL respectively (see Examples 4b and 4d of WO 2007/144005 A1, respectively). As vortioxetine hydrobromide also exists in hydrated forms (e.g. the hemihydrate of Examples 4g and 4h of WO 2007/144005 A1, and the novel hydrate of the present invention) solubility determinations in aqueous solvent systems (as applied in WO 2007/144005 A1) should be avoided as an initially applied anhydrous form might transform, at least partially, to a hydrated form during the determinations, which might distort the results.

It is known to a person skilled in the art that the difference in the relative solubility of two polymorphs is independent from the solvent system, if an "ideal solution", meaning a solution which is not too concentrated, is present. (see e.g. Kuhnert-Brandstätter M., Burger A., Pharmazeutische Industrie, 1972, 34, Nr. 3, 187-190; Samuel H. Yalowsky, Solubility and Solubilization in Aqueous Media, ACS, Oxford University Press 1999, ISBN: 0-8412-3576-7, p. 98). Therefore the solubilities of vortioxetine hydrobromide forms alpha and beta of WO 2007/144005 A1 and the compound of the present invention were determined in a mixture of hexanol and n-heptane. In this particular solvent system all three polymorphs remained stable, meaning they did not transform into other forms during the solubility determination, which was confirmed by XRPD. In addition the solubility in this solvent system was low enough for all three polymorphs to ensure the presence of an "ideal solution". The relative solubilities of polymorphs alpha:beta:delta were found to be 2.1:1.0:3.2. (see example 4 of the present invention).

Once knowing the relative solubilities of polymorphs alpha, beta and the compound of the present invention, the water solubilities of the polymorphs was calculated based on the water solubility data provided in WO 2007/144005 A1 for forms alpha and beta. On the one hand the water solubility of form alpha (2.0 mg/mL) disclosed in WO 2007/144005 A1 was used as a basis for the calculation (table 1, column 3), and on the other hand the water solubility of form beta (1.2 mg/mL) disclosed in WO 2007/144005 A1 was used for the calculation (table 1 column 4). Table 1 shows the calculated water solubilities of polymorphs alpha, beta and the compound of the present invention.

TABLE 1

Calculated water solubilities for polymorphs alpha, beta and the crystalline compound of the present invention

| polymorph | relative solubility [mg/ml] | calculated water solubility[1] [mg/ml] | calculated water solubility[2] [mg/ml] |
| --- | --- | --- | --- |
| alpha | 2.1 | _2.0_ | 2.5 |
| beta | 1.0 | 1.0 | _1.2_ |
| compound of the present invention | 3.2 | 3.0 | 3.8 |

[1]calculation with water solubility value of polymorph apha from WO 2007/144005 A1
[2]calculation with water solubility value for polymorph beta from WO 2007/144005 A1

Unexpectedly, the compound of the present invention shows higher solubility than forms alpha and beta of WO 2007/144005 A1. Hence, the crystalline compound of the present invention is especially suitable for the preparation of an orally administered medicament as the oral bioavailability is expected to be higher than that for polymorphs alpha and beta.

According to page 7, lines 3-5 of WO 2007/144005 A1, form beta has an attractive combination of solubility and low hygroscopicity, allegedly making this polymorph especially suited for making tablets. Unexpectedly, the crystalline compound of the present invention shows even a more attractive combination of high solubility and low hygroscopicity and is therefore the most suitable crystalline form of vortioxetine hydrobromide for making tablets.

In summary, solvates are no suitable forms for the preparation of a medicament due to the strict limits for residual solvents. In addition, the crystalline compound of the present invention shows (compared to forms alpha, beta, gamma and the hemihydrate of WO 2007/144005 A1) the most attractive combination of low hygroscopicity (positively affecting the storage stability) and high solubility (positively affecting the bioavailability) and is therefore the most favored form for the preparation of a solid medicament.

It is further believed that the crystalline compound of the present invention is stably present in a solid finished dosage form over a long period of time (even at high temperature and high relative humidity), such that the chemical and physical quality during the shelf-life of the solid finished dosage form containing the crystalline compound is ensured. Special and expensive packaging can then be avoided.

Finally, the crystalline forms alpha, beta and the ethyl acetate solvate of WO 2007/144005 A1 as well as the crystalline form gamma and the hemihydrate of WO 2007/144005 A1 are difficult to make in a reliable manner because these forms are obtained via crystallizations from the same solvent systems. As the ethyl acetate solvate and the polymorphs alpha and beta are all obtained via crystallizations from ethyl acetate and the form gamma and the hemihydrate are both obtained via crystallizations from water, the production processes are especially critical and sensitive. In particular, these crystalline forms can only be obtained in pure form in a quite narrow range of critical parameters, such as the crystallization temperature, the concentration and the stirring time (as described in the concrete examples 4a, 4c, 4e, 4g and 4i of WO 2007/144005 A1). In contrast, the novel polymorph of vortioxetine hydrobromide of the present invention can be obtained in polymorphically pure form in a reliable manner by applying the novel hydrate of the present invention as an intermediate in the process for the production of the novel polymorph. The novel hydrate of the present invention is the only form obtained via evaporation of an aqueous ethanolic or methanolic solution of vortioxetine hydrobromide at room temperature and can thus be transformed to the novel crystalline compound of the present invention in a straight forward manner.

Hence the present invention overcomes the drawbacks of the known crystalline forms of vortioxetine hydrobromide, such as the forms disclosed in WO 2007/144005 A1 and WO 2010/094285 A1, respectively. In particular, such drawbacks include toxicity issues of solvates, stability issues due to water uptake, bioavailability issues due to limited solubility and/or preparation issues due to similar crystallization processes. These and other drawbacks are overcome by providing a non-solvated crystalline form of vortioxetine hydrobromide which is non-hygroscopic, shows high solubility and can be obtained in polymorphically pure form in an economic and reliable manner.

Thus, the crystalline compound of the present invention is the most favored form for oral solid pharmaceutical compositions, and may advantageously be employed in various pharmaceutical formulations for use in the treatment of several indications, such as mood disorders (e.g., depression and anxiety) and also for the treatment of cognitive impairment and pain. The present invention therefore also relates to pharmaceutical compositions comprising the crystalline compound of the present invention as described above and a pharmaceutically acceptable carrier.

The crystalline compound of the present invention may further be employed in pharmaceutical formulations for use in the treatment of several further indications, including chronic pain including phantom limb pain, neuropathic pain, diabetic neuropathy, post-herpetic neuralgia (PHN), carpal tunnel syndrome (CTS), HIV neuropathy, complex regional pain syndrome (CPRS), trigeminus neuralgia, tic douloureux, surgical intervention (e.g. post-operative analgesics), diabetic vasculopathy, capillary resistance, diabetic symptoms associated with insulitis, pain associated with menstruation, pain associated with cancer, dental pain, headache, migraine, tension-type headache, trigeminal neuralgia, temporomandibular joint syndrome, myofascial pain, muscular injury, fibromyalgia syndrome, bone and joint pain (osteoarthritis), rheumatoid arthritis, rheumatoid arthritis and edema resulting from trauma associated with burns, strains or fracture bone pain due to osteoarthritis, osteoporosis, bone metastases or unknown reasons, gout, fibrositis, myofascial pain, thoracic outlet syndromes, upper back pain or lower back pain (wherein the back pain results from systematic, regional, or primary spine disease (radiculopathy), pelvic pain, cardiac chest pain, non-cardiac chest pain, spinal cord injury (SCI)-associated pain, central post-stroke pain, cancer neuropathy, AIDS pain, sickle cell pain or geriatric pain. In one embodiment, pain is irritable bowl syndrome (IBS).

The crystalline compound of the present invention may further be employed in pharmaceutical formulations for use in the treatment of mood disorders, such as depression and anxiety, abuse (alcohol, narcotics etc) or chronic pain disorders.

Further potential indications include circadian rhythm disorder, sleep disorders, sleep-disordered breathing; hypopnea syndrome; abdominal pain; depression, in particular severe depression; dysthymic disorder; cyclothymia; exhaustive depression; atypical depression; mood disorder associated with a generalised medical disorder; substance induced mood disorder; recurrent depression, single episode depression; paediatric depression; post-stroke depression; peri-, pre- or post-menupausal dysphoric disorder; seasonal affective disorder (SAD); aggression and agitation in dementia, such as Alzheimer's; compulsive and attention spectrum disorders in ADHD, autism and Asperger's syndrome; leucariosis, small vessel disease, depression associated with abuse, irritability, hostility, sleep disorders, fatigue, Huntington's disease, multiple sclerosis, anxiety (anxious depression) and pain, in particular pain in the gastrointestinal tract, such as e.g. irritable bowl syndrome (IBS); general anxiety disorder associated with pain; impulse control disease; intermittent explosive disorder; kleptomania; pyromania; pathological gambling; trichotillomania; negative symptoms of schizophrenia; mild cognitive impairment; vascular dementia; cognitive impairment associated with Down's syndrome, tph gene mutations, ADHD, epilepsy, traumatic brain injury or Asperger's syndrome; compulsive and attention spectrum disorder in ADHD, Asperger's syndrome and autism; aggression and agitation in dementia and Alzheimer's, disease; chronic fatigue syndrome; stress related disorder, acute stress; stress; burn-out; insulin resistance associated with HPA-axis hyperactivity; eating disorder, such as obesity, binge eating, anorexia and bulimia nervosa; conduct disorder; behavioural disturbances; behavioural disturbances associated with dementia; fear of flying; fear of elevators; fear of small rooms; and amblyopia.

Preferably the present invention relates to pharmaceutical compositions, wherein more than 95% of vortioxetine hydrobromide is stably present as the crystalline compound of the present invention, more preferably wherein the crystalline compound of the present invention is the only detectable crystalline form of vortioxetine hydrobromide. The absence of other crystalline forms of vortioxetine hydrobromide, such as forms alpha, beta, gamma, the hemihydrate and the ethyl acetate solvate of WO 2007/144005 A1, the isopropanol solvate of WO 2010/094285 A1 or the monohydrate of the present invention can be tested by comparing an XRPD taken of any crystalline vortioxetine hydrobromide with the XRPD of form delta as obtained e.g. from example 1 and shown in FIG. 1, which for this comparison can be taken as an XRPD of 100% crystalline compound of the present invention.

The main characteristics of diffraction line profiles are 2θ position, peak height, peak area and shape (characterized by, for example, peak width or asymmetry, analytical function, empirical representation). In addition to the diffraction peaks, an X-ray diffraction experiment also generates a more-or-less uniform background, upon which the peaks are superimposed. Besides specimen preparation, other factors contribute to the background, for instance the sample holder, diffuse scattering from air and equipment, other instrumental parameters such as detector noise, general radiation from the X-ray tube, etc. The peak-to-background ratio can be increased by minimizing background and by choosing prolonged exposure times. In the context of the present invention, the term "peak" denotes a particular 2θ position, wherein the signal-to-noise ratio (calculated according to item 2.2.46 of the European Pharmacopoeia) is greater than 3/1. "Absence of a peak" is herein defined as a peak having an intensity of at most 1%, such as 0.5% or 0.2%, of the highest peak in an XRPD of a sample of vortioxetine hydrobromide, more preferably no detectable XRPD peak above background signals.

"Stably present" as defined herein means that even after storage of the pharmaceutical composition for 180 days, and preferably even after storage for 3 years, the crystalline form of vortioxetine hydrobromide designated as crystalline compound of the present invention initially comprised in the pharmaceutical composition is still present as crystalline compound of the present invention after storage for the indicated period.

The pharmaceutical compositions of the present invention comprising the crystalline compound of the present invention may further comprise one or more pharmaceutically acceptable excipients. Such excipients are preferably selected from the group consisting of diluents, sweeteners, buffering agents, glidants, flowing agents, flavouring agents, lubricants, preservatives, surfactants, wetting agents, binders, disintegrants and thickeners. Other excipients known in the field of pharmaceutical compositions may also be used. Furthermore the pharmaceutical composition may comprise a combination of two or more excipients also within one of the members of the above mentioned group.

Suitable wetting agents which can be used for the pharmaceutical compositions of the present invention comprising the crystalline compound of the present invention, comprise e.g. sodium lauryl sulphate, sodium dioctyl sulfosuccinate, sodium starch glycolate or wetting agents belonging to the group of the polyethylene glycol sorbitan fatty acid esters, such as wetting agents known as Tween, e.g. Tween 20, 60 and 80.

Suitable binders which can be used for the pharmaceutical compositions of the present invention comprising the crystalline compound of the present invention, further comprise e.g. alkylcelluloses such as methylcellulose, hydroxyalkylcelluloses such as hydroxymethylcellulose, hydroxyethylcellulose, hydroxypropylcellulose and hydroxybutylcellulose, hydroxyalkylalkylcelluloses such as hydroxyethylmethylcellulose and hydroxypropylmethylcellulose, carboxyalkylcelluoses such as carboxymethylcellulose, alkali metal salts of carboxyalkylcelluloses such as sodium carboxymethylcellulose, carboxyalkylalkylcelluloses such as carboxymethylethylcellulose, carboxyalkylcellulose esters, starches such as starch 1551, pectins such as sodium carboxymethylamylopectin, chitin derivatives such as chitosan, heparin and heparinoids, polysaccharides such as alginic acid, alkali metal and ammonium salts thereof, carrageenans, galactomannans, tragacanth, agar-agar, gum arabic, guar gum and xanthan gum, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, polyalkylene oxides such as polyethylene oxide and polypropylene oxide and copolymers of ethylene oxide and propylene oxide, e.g. poloxamers and poloxamines, copovidone.

Suitable diluents which can be used for the pharmaceutical compositions of the present invention comprising the crystalline compound of the present invention further comprise e.g. calcium carbonate, dibasic calcium phosphate, dibasic calcium phosphate dihydrate, tribasic calcium phosphate, calcium sulphate, microcrystalline cellulose including silicified microcrystalline cellulose, powdered cellulose, dextrates, dextrin, dextrose excipient, fructose, kaolin, lactitol, lactose anhydrous, lactose monohydrate, mannitol, sorbitol, starch, modified starch, sodium chloride, sucrose, compressible sugar, confectioner's sugar, a spray-dried mixture of lactose monohydrate and microcrystalline cellulose (75:25), commercially available as Microcelac®, a co-processed spray-dried mixture of microcrystalline cellulose and colloidal silicon dioxide (98:2), commercially available as Prosolv®.

Suitable glidants which can be used for the pharmaceutical compositions of the present invention comprising the crystalline compound of the present invention further comprise e.g. talc, colloidal silicon dioxide, starch and magnesium stearate.

Suitable disintegrants which can be used for the pharmaceutical compositions of the present invention comprising the crystalline compound of the present invention further comprise e.g. starch, ion exchange resins, e.g. Amberlite, cross-linked polyvinylpyrrolidone, modified cellulose gum, e.g croscarmellose sodium, sodium starch glycolate, sodium carboxymethylcellulose, sodium dodecyl sulphate, modified corn starch, microcrystalline cellulose, magnesium aluminium silicate, alginic acid, alginate and powdered cellulose.

Suitable lubricants which can also be used for the pharmaceutical compositions of the present invention comprising the crystalline compound of the present invention further comprise e.g. magnesium stearate, calcium stearate, stearic acid, talc, polyethylene glycol, sodium lauryl sulphate and magnesium lauryl sulphate.

In addition the pharmaceutical compositions of the present invention comprising crystalline compound of the present invention may further comprise other optional excipients such as, for example, flavours, sweeteners and colouring agents.

A preferred tablet of the present invention comprises a tablet core comprising the crystalline compound of the present invention, mannitol, microcrystalline cellulose, sodium starch glycolate, hydroxypropylmethyl cellulose and magnesium stearate.

Another preferred tablet of the present invention comprises a tablet core comprising the crystalline compound of the present invention, lactose monohydrate, silicified microcrystalline cellulose, croscarmellose sodium, polysorbate 20 (Tween 20), polyvinylpyrrolidone K30 (PVP K30) and magnesium stearate.

A further preferred tablet of the present invention comprises a tablet core comprising the crystalline compound of the present invention, microcrystalline cellulose, polysorbate 20 (Tween 20), polyvinylpyrrolidone K30 (PVP K30), dibasic calcium phosphate (dihydrate or anhydrate e.g. Emcompress® or anhydrous Emcompress®), magnesium stearate and starch.

In addition a preferred tablet of the present invention comprises a tablet core comprising the crystalline compound of the present invention, microcrystalline cellulose, lactose monohydrate, polysorbate 20 (Tween 20), polyvinylpyrrolidone K30 (PVP K30), magnesium stearate and starch.

Another preferred tablet of the present invention comprises a tablet core comprising the crystalline compound of the present invention, microcrystalline cellulose, modified starch, polysorbate 20 (Tween 20), polyvinylpyrrolidone K30 (PVP K30) and magnesium stearate.

In one embodiment, suitable tablets may be composed as follows—percentages indicated are w/w-%:

| | |
|---|---|
| 3-8% | crystalline compound of the present invention |
| 35-45% | anhydrous calcium hydrogen phosphate |
| 15-25% | corn starch |
| 2-6% | copovidone |
| 20-30% | microcrystalline cellulose |
| 1-3% | sodium starch glycolate |
| 2-6% | talc |
| 0.5-2% | magnesium stearate |

In another embodiment, suitable tablets may be composed as follows—percentages indicated are w/w-%:

| | |
|---|---|
| approximately 5% | crystalline compound of the present invention |
| approximately 39% | anhydrous calcium hydrogen phosphate |
| approximately 20% | corn starch |
| approximately 3% | copovidone |
| approximately 25% | microcrystalline cellulose |
| approximately 3% | sodium starch glycolate |
| approximately 4% | talc |
| approximately 1% | magnesium stearate |

Tablets with different amounts of active compound, such as corresponding to e.g. 2.5, 5, 10, 20, 25, 30, 40, 50, 60 or 80 mg of the free base may be obtained by choosing the right amount of the crystalline compound of the present invention in combination with a tablet of an appropriate size.

Conveniently, the crystalline compound of the present invention is administered in unit dosage form containing said compound in an amount of about 1 to 50 mg. The total daily dose is usually in the range of about 1-20 mg, such as about 1 to 10 mg, about 5-10 mg, about 10-20 mg, or about 10-15 mg of the compound of the invention. Particular mention is made of daily doses of 2.5, 5, 10, 15 or 20 mg.

In one embodiment a tablet of the present invention may be prepared by wet granulation, preferably comprising the steps of:
a) dry blending the crystalline compound of the present invention and a part of the diluent,
b) preparing a binder solution by dissolving a binder and a wetting agent in a suitable solvent,
c) spraying the binder solution of step b) on the mixture obtained in step a),
d) drying the obtained granulate and sieving the same,
e) mixing the obtained granulate with the remaining part of diluent and a disintegrant,
f) adding an optional glidant and/or an optional lubricant to the mixture,
g) compressing the obtained mixture into a tablet and
h) film-coating the obtained tablet.

Suitable solvents in step b) of the herein disclosed wet granulation process are e.g. water, acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate and tetrahydrofuran.

A particular tablet of the present invention may be prepared by wet granulation comprising the steps of:
a) dry blending the crystalline compound of the present invention and mannitol,
b) preparing a binder solution by dissolving hydroxypropylmethyl cellulose and sodium starch glycolate in a suitable solvent,
c) spraying the binder solution of step b) on the mixture obtained in step a),
d) drying the obtained granulate and sieving the same,
e) mixing the obtained granulate with microcrystalline cellulose
f) adding magnesium stearate to the mixture,
g) compressing the obtained mixture into a tablet and
h) film-coating the obtained tablet.

Suitable solvents in step b) of the herein disclosed wet granulation process are e.g. water, acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate and tetrahydrofuran.

Formulations of the present invention typically comprise about 5 to 50 mg, preferably about 5 to 25 mg, more preferably about 5 to 15 mg and most preferably about 5 to 10 mg the crystalline compound of the present invention (calculated as vortioxetine free base).

Exemplary processes for producing suitable formulations are disclosed in Examples 15a to 15i of WO 2007/144005 A1.

In a second aspect the present invention relates to a novel crystalline hydrate of vortioxetine hydrobromide.

The novel hydrate can be identified via a monoclinic unit cell having space group $P2_1/c$.

Preferably, these monoclinic unit cells are characterized by the following parameters as determined by X-ray structural analysis:
a=37.33+/−0.6 Å
b=6.46+/−0.1 Å
c=31.36+/−0.5 Å
α=90°
β=94.9°+/−0.5°
γ=90°
Z=16

In particular, these monoclinic unit cells are characterized by the following parameters as determined by X-ray structural analysis:
a=37.333 Å
b=6.464 Å
c=31.361 Å
α=90°
β=94.90°
γ=90°
Z=16

The novel hydrate of the present invention can further be characterized by showing an X-ray powder diffractogram comprising characteristic peaks (expressed in 2θ±0.2° 2θ (CuKα radiation)) at 4.7°, 14.0°, 19.9° and 20.5°. The X-ray powder diffractogram of the novel hydrate of the present invention comprises additional characteristic peaks at 2-theta angles of 5.6°, 8.7°, 9.4°, 14.4°, 15.4°, 16.3°, 16.9°, 17.2°, 17.7°, 18.2°, 19.6°, 21.0°, 21.5°, 22.0°, 22.3°, 22.6°, 22.8°, 23.6°, 23.8°, 24.9°, 25.4°, 27.7°, 28.0°, 28.5°, 29.8° and 32.6° (expressed in 2θ±0.2° 2θ (CuKα radiation)).

Figure 9:
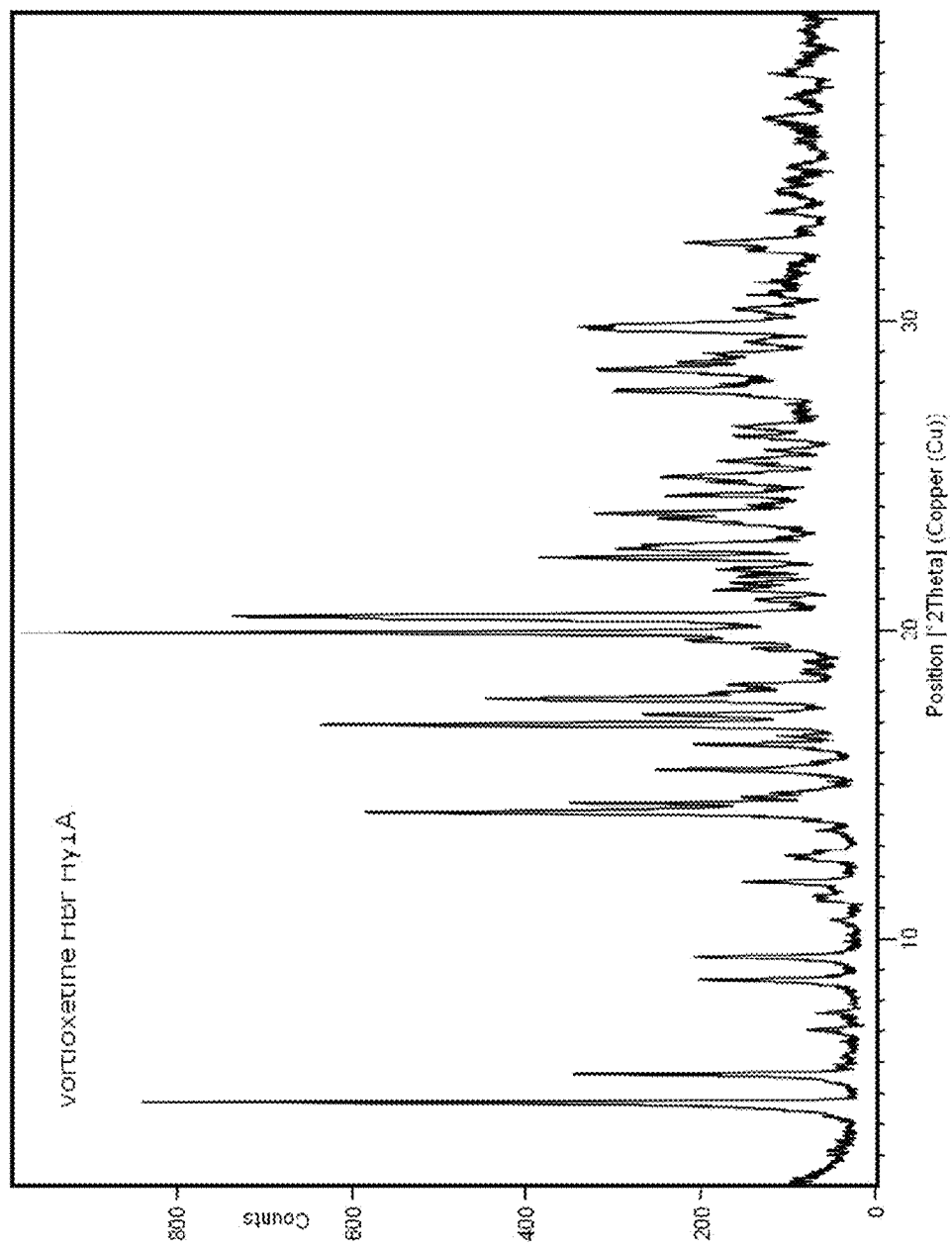
FIG. 9: X-ray powder diffractogram (XRPD) of vortioxetine hydrobromide hydrate form of the present invention

The novel hydrate of the present invention can be characterized by showing an X-ray powder diffractogram (expressed in 2θ±0.2° 2θ (CuKα radiation)) as shown in FIG. 9. The X-ray powder diffractogram of the novel hydrate of the present invention comprises the following characteristic peaks (expressed in 2θ±0.2° 2θ (CuKα radiation)) of 4.7°, 5.6°, 7.6°, 8.7°, 9.4°, 14.0°, 14.4°, 15.4°, 16.3°, 16.9°, 17.2°, 17.7°, 18.2°, 19.6°, 19.9°, 20.5°, 21.0°, 21.5°, 22.0°, 22.3°, 22.6°, 22.8°, 23.6°, 23.8°, 24.9°, 25.4°, 26.5°, 27.7°, 28.0°, 28.5°, 29.8° and 32.6°.

Figure 10:
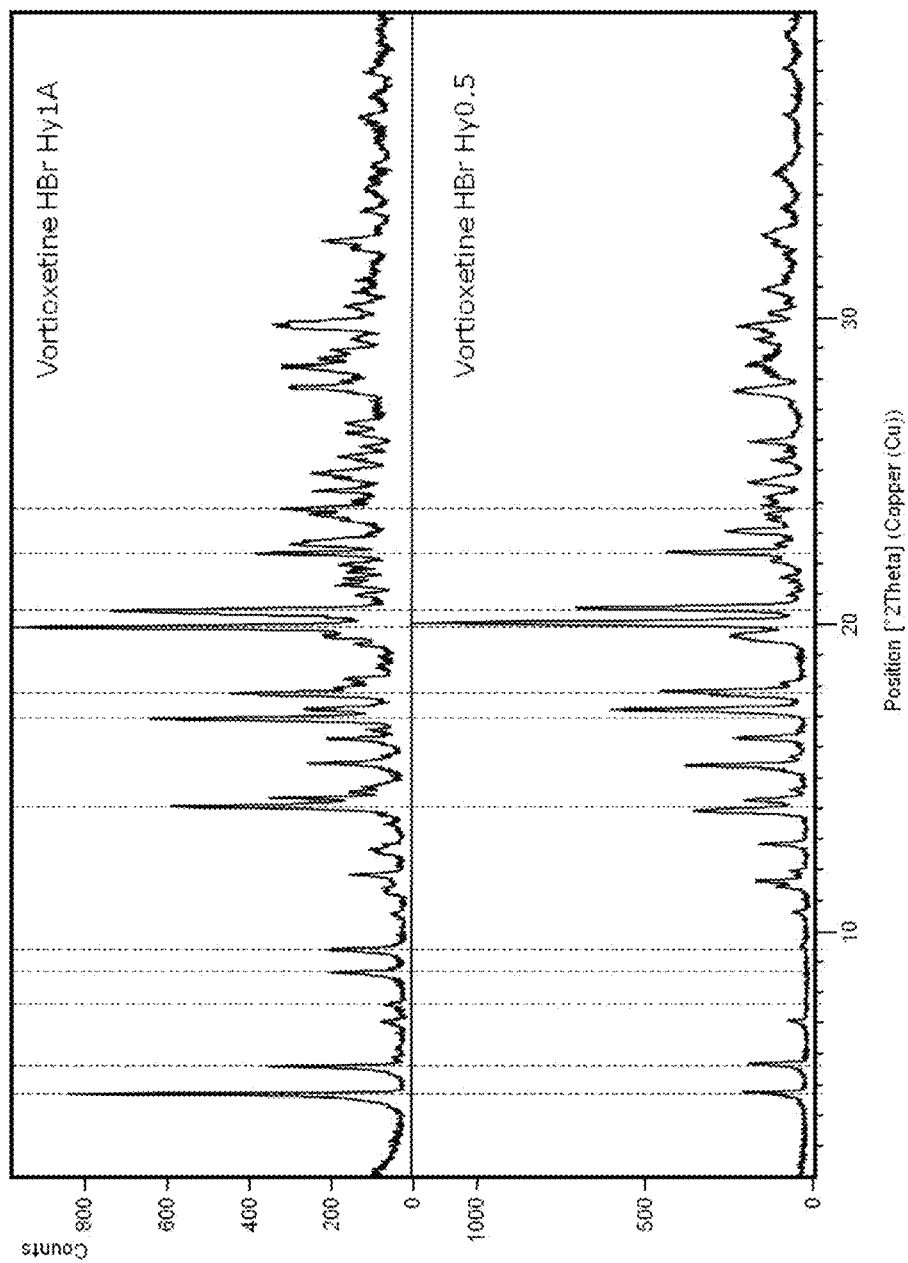
FIG. 10: Comparison of X-ray powder diffractograms of vortioxetine hydrobromide hydrate form of the present invention (above) and vortioxetine hydrobromide hemihydrate form of WO 2007/144005 A1 (below)

When the X-ray powder diffractogram of the novel hydrate of the present invention is compared to the diffractogram of the hemihydrate of WO 2007/144005 A1, several differences can be observed as shown in FIG. 10. For instance, the novel hydrate of the present invention exerts peaks at 2-theta angles of 7.6°, 8.7°, 9.4° and 26.5° that cannot be found in the diffractogram of the hemihydrate form disclosed in WO 2007/144005 A1. Conversely, some of the peaks at 2-theta angles, e.g. 10.7°, 11.7°, 15.4°, 17.9°, are characteristic for the hemihydrate only.

Figure 11:
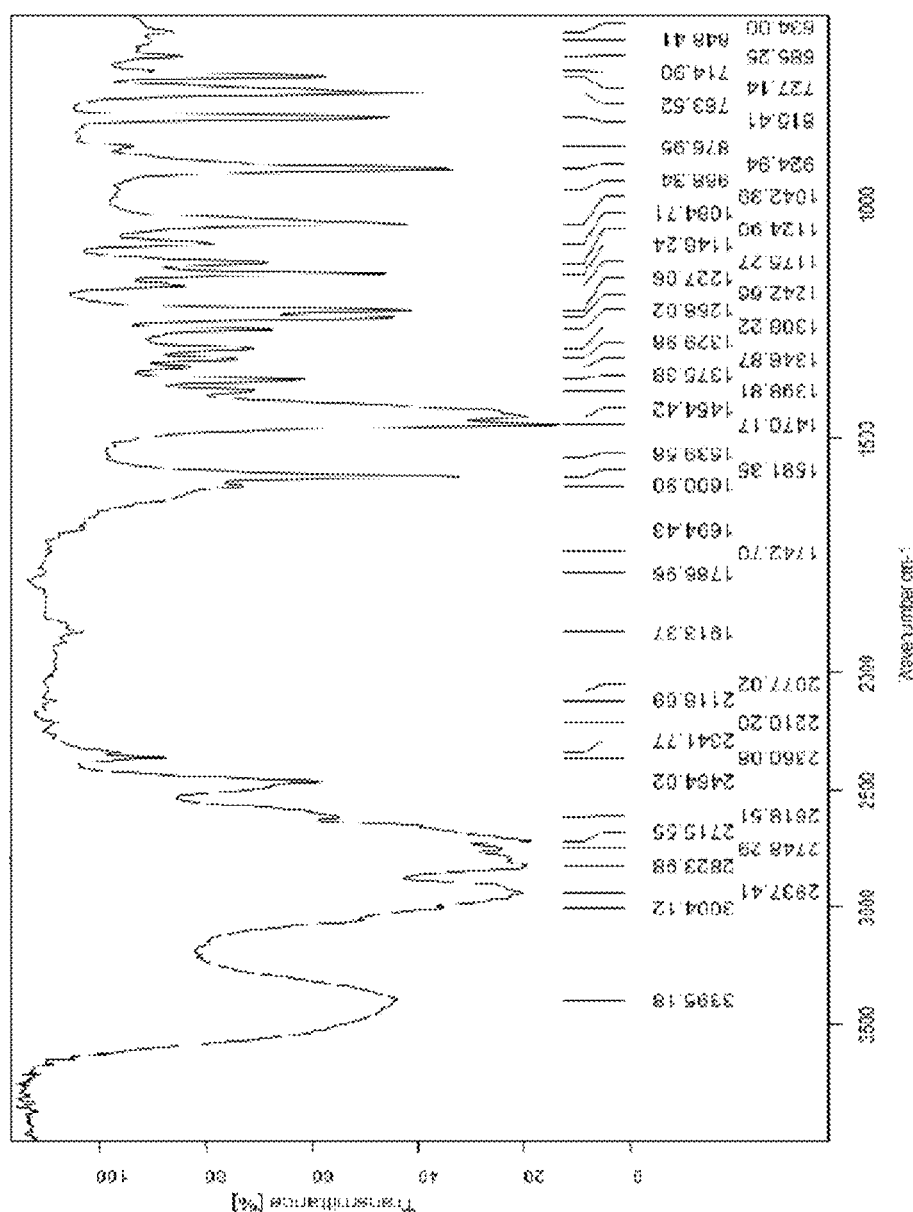
FIG. 11: Fourier transform infrared (FTIR) spectrum of vortioxetine hydrobromide hydrate form of the present invention
Figure 12:
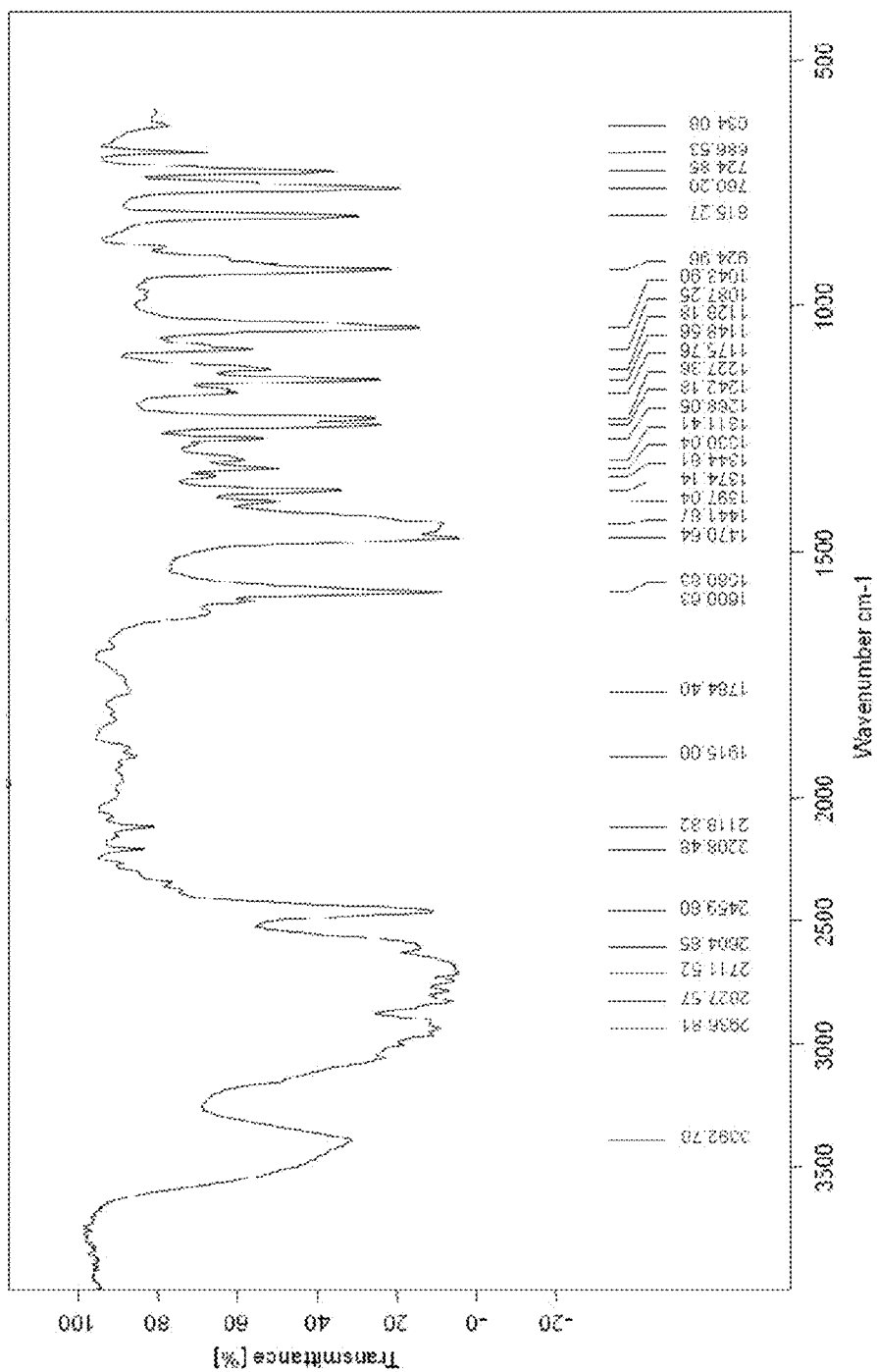
FIG. 12: Fourier transform infrared (FTIR) spectrum of vortioxetine hydrobromide hemihydrate form of WO 2007/144005 A1

Moreover, a comparison of solid state mid-IR data shows clear differences between the novel hydrate of the present invention (FIG. 11) and the hemihydrate of WO 2007/144005 A1 (FIG. 12), in several regions. Specifically in the 2800-2600 cm$^{-1}$ (amine salt), 1610-1590 cm$^{-1}$ (water bending vibration region), 1120-1030 and 770-720 cm-1 (aromatic CH region). The differences in the vibrational frequencies clearly reflect structural differences between the two crystal structures.

The hydrate of vortioxetine hydrobromide prepared according to the process of the present invention preferably comprises about 0.8 to 1.2 mols water, more preferably about 0.9 to 1.1 mols water and most preferably about 1.0 mol water per mol vortioxetine hydrobromide. For instance, Karl Fischer titration of a representative sample resulted in about 4% of water which corresponds to 0.9 mol of water per mol vortioxetine hydrobromide. The hydrate of WO 2007/144005 A1 is described to be a hemihydrate (see e.g. example 4h of WO 2007/144005 A1 "Characterisation of the hemi hydrate of the hydrobromide of compound I") and is therefore significantly different from the monohydrate of the present invention.

In a further embodiment the present invention relates to a process for the preparation of the novel monohydrate of vortioxetine hydrobromide comprising the step of evaporating an aqueous alcoholic solution of vortioxetine hydrobromide at room temperature and recovering the crystals.

Any form of vortioxetine hydrobromide can be applied in the process e.g. crystalline vortioxetine hydrobromide, amorphous vortioxetine hydrobromide or mixtures thereof. Suitable crystalline forms are e.g. forms alpha, beta and gamma of WO 2007/144005 A1 or crystalline form delta of the present invention or mixtures thereof. The free base of vortioxetine may be prepared as disclosed in WO 2003/029232 A1. Salts of vortioxetine may be prepared by dissolving the free base in an appropriate solvent, adding the relevant acid, followed by precipitation (the preparation of several solid forms of vortioxetine hydrobromide is disclosed e.g. in WO 2007/144005 A1). Precipitation may be accomplished either by the addition of a second solvent, and/or evaporation, and/or cooling. Alternatively, the free base of vortioxetine may be synthesized in a palladium catalyzed reaction as described in WO 2007/144005 A1.

In a first step, the applied vortioxetine hydrobromide starting material is dissolved in an aqueous alcohol upon heating. Suitable alcohols are $C_1$-$C_2$ alcohols such as methanol or ethanol. The applied alcohol preferably has a concentration ranging from about 50 to 96%, more preferably from about 50 to 80% and most preferably from about 50 to 65%.

Depending on the initial vortioxetine hydrobromide concentration and the solvent applied the dissolution temperature may range from e.g. room temperature to reflux temperature. The initial vortioxetine hydrobromide concentration preferably ranges from about 5 to 100 g/L, more preferably from about 5 to 75 g/L and most preferably from about 5 to 50 g/L.

After the vortioxetine hydrobromide starting material dissolved, an optional filtration step may be applied, wherein the solution may be treated with charcoal prior to the filtration step.

Thereafter the solution is cooled to room temperature at a cooling rate preferably ranging from about 0.1° C./min to 10.0° C./min, more preferably from about 0.3° C./min to 5.0° C./min and most preferably from about 0.5° C./min to 2.0° C./min. Finally the solution is allowed to evaporate at ambient conditions and the solid material is collected.

The novel hydrate of vortioxetine hydrobromide is not stable at room temperature and converts to form alpha of WO 2007/144005 A1 within about 4 weeks. However, unexpectedly, heating the monohydrate above about 120° C. does not lead to form alpha but to the novel crystalline compound of the present invention.

Hence, the novel hydrate of vortioxetine hydrobromide of the present invention is a valuable intermediate for the preparation of the crystalline compound of the present invention. The hydrate of the present invention may be transformed to the compound of the present invention according to the process disclosed for said form production, in which the hydrate of the present invention is heated to a temperature ranging from about 120 to 150° C., preferably from about 120 to 140° C. for a certain period of time, preferably for at least 2, 4, or 6 hours.

Hence, the present invention further relates to a crystalline compound comprising a hydrobromic acid (HBr) salt of a compound of formula I (1-{2-[(2,4-dimethylphenyl)sulfanyl]phenyl}piperazine, INN: vortioxetine),

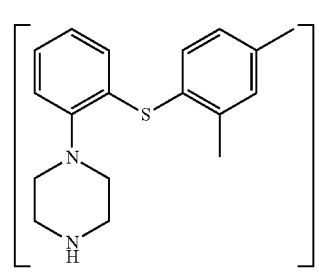

formula I obtainable by heating the hydrate of the present invention to a temperature ranging from about 120 to 150° C., preferably from about 120 to 140° C. for a certain period of time, preferably for at least 2, 4, or 6 hours.

The present invention further relates to a crystalline compound comprising a hydrobromic acid (HBr) salt of a compound of formula I (1-{2-[(2,4-dimethylphenyl)sulfanyl]phenyl}piperazine, INN: vortioxetine),

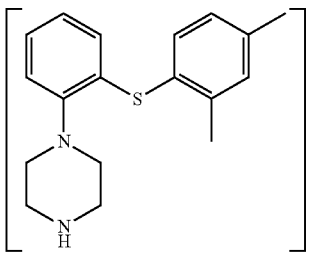

formula I obtainable by
(a) evaporating an aqueous alcoholic solution of vortioxetine hydrobromide at room temperature and recovering the crystals, wherein the alcohol in the aqueous alcoholic solution is selected from methanol, ethanol or mixtures thereof; and
(b) heating the recovered crystals of (a) to a temperature ranging from about 120 to 150° C., preferably from about 120 to 140° C. for a certain period of time, preferably for at least 2, 4, or 6 hours.

The present invention further relates to a crystalline hydrate of vortioxetine hydrobromide, obtainable by evaporating an aqueous alcoholic solution of vortioxetine hydrobromide at room temperature and recovering the crystals, wherein the alcohol in the aqueous alcoholic solution is selected from methanol, ethanol or mixtures thereof.

Therefore the present invention also relates to the use of the novel crystalline hydrate of vortioxetine hydrobromide of the present invention as an intermediate for the preparation of the crystalline compound of the present invention.

In addition the present invention relates to the use of the novel crystalline hydrate of vortioxetine hydrobromide of the present invention as an intermediate for the preparation of vortioxetine hydrobromide form alpha of WO 2007/144005 A1.

In the following the present invention will be described in further detail by illustrative, non-limiting examples.

EXAMPLES

The X-ray powder diffractograms (XRPD) were obtained with an X'Pert PRO diffractometer (PANalytical, Almelo, The Netherlands) equipped with a theta/theta coupled goniometer in transmission geometry, programmable XYZ stage with well plate holder, Cu-Kα1,2 radiation source (wavelength 0.15419 nm) and a solid state PIX'cel detector. The diffractograms were recorded at a tube voltage of 40 kV, tube current of 40 mA. A typical precision of the 2-theta values is in the range of about ±0.2° 2-theta. Thus a diffraction peak that appears at 5.0° 2-theta can appear between 4.8 and 5.2° 2-theta on most X-ray diffractometers under standard conditions.

Intensity data for the crystal structure were collected with Mo ($\lambda$=0.71073 Å) radiation on an Oxford Diffraction Gemini-R Ultra diffractometer at 173 K. The structure was solved using the direct methods procedure in SHELXS97 and refined by full-matrix least squares on $F^2$ using SHELXL97.

The Fourier transform infrared (FTIR) spectrum was recorded with a Bruker IFS 25 spectrometer (Bruker GmbH, Karlsruhe, D) in the spectral range from 4000 to 600 $cm^{-1}$. The sample was prepared on a ZnSe disk using the Bruker IR microscope I, with 15x-Cassegrain-objectives. A typical precision of the wavenumber values is in the range of about ±2 $cm^{-1}$. Thus an infrared peak that appears at 1716 $cm^{-1}$ can appear between 1714 and 1718 $cm^{-1}$.

Thermogravimetric analysis (TGA) was performed with a TGA 7 thermogravimetric system (Perkin-Elmer). The sample was placed into a 50 μL platinum pan and heated at a heating rate of 10° C./min. The determination was performed under nitrogen purge (balance purge: 40 mL/min, sample purge: 20 mL/min).

Gravimetric moisture sorption/desorption curves were acquired using a SPS-11 moisture sorption analyzer (MD Messtechnik, Ulm, D). The measurement cycle was started at 43% relative humidity (RH) and decreased in 10% steps down to 0% RH; up to 95% RH, down to 0% RH and up to 43% RH. The equilibrium condition for each step was set to a mass constancy of ±0.01% over 30 min. The temperature was 25±0.1° C.

The KF-Coulometer DL37 (Mettler-Toledo AG, Greifensee, CH) with a double-platinum-detecting electrode and pyridine-free Karl Fischer reagent 1.09255.0500 (Merck, Darmstadt, D) was used for the coulometric water determination of the samples.

Example 1

Preparation of the Compound of the Present Invention (Vortioxetine Hydrobromide)

54 mg vortioxetine hydrobromide monohydrate of the present invention (e.g. obtained according to examples 2 or 3 of the present invention) were dried at 130° C. under vacuum (<15 mbar) for 4 hours to obtain the crystalline compound of the present invention (vortioxetine hydrobromide).

TABLE 2

XRPD angles 2-theta and relative intensities of the crystalline compound of the present invention prepared according to example 1

| angle [2-theta] | relative intensity [%] |
|---|---|
| 5.5 | 42 |
| 12.2 | 24 |
| 13.7 | 27 |
| 14.5 | 23 |
| 14.8 | 31 |
| 16.2 | 23 |
| 16.7 | 29 |
| 20.0 | 100 |
| 20.7 | 27 |
| 22.4 | 27 |
| 22.8 | 22 |
| 23.7 | 24 |
| 24.6 | 25 |
| 25.6 | 26 |
| 27.6 | 28 |
| 28.1 | 28 |
| 28.4 | 28 |
| 28.6 | 29 |
| 29.1 | 29 |
| 30.5 | 30 |
| 34.4 | 34 |

TABLE 3

FTIR peaks of the crystalline compound of the present invention prepared
according to example 1

| wavenumber [cm$^{-1}$] |
| --- |
| 3166 |
| 2959 |
| 2931 |
| 2786 |
| 2753 |
| 2713 |
| 2621 |
| 2596 |
| 2484 |
| 2472 |
| 1601 |
| 1586 |
| 1471 |
| 1454 |
| 1438 |
| 1398 |
| 1375 |
| 1346 |
| 1329 |
| 1312 |
| 1267 |
| 1243 |
| 1227 |
| 1149 |
| 1122 |
| 1081 |
| 1043 |
| 925 |
| 910 |
| 873 |
| 813 |
| 764 |
| 725 |
| 685 |
| 629 |

Example 2

Preparation of the Hydrate of Vortioxetine Hydrobromide

A mixture of 118 mg vortioxetine hydrobromide form alpha (e.g. obtained as described in Example 4a of WO 2007/144005) in 4 mL ethanol (50 volume %) was heated to 70° C., whereat a clear solution was obtained. The solution was allowed to cool to room temperature. After evaporation at ambient conditions vortioxetine hydrobromide hydrate was obtained.

Example 3

Preparation of the Hydrate of Vortioxetine Hydrobromide

A mixture of 55 mg vortioxetine hydrobromide form alpha (e.g. obtained as described in Example 4a of WO 2007/144005) in 4 mL methanol (50 volume %) was heated to 60° C., whereat a clear solution was obtained. The solution was allowed to cool to room temperature. After evaporation at ambient conditions vortioxetine hydrobromide hydrate was obtained.

Example 4

Solubilities of Polymorphs Alpha, Beta of Vortioxetine Hydrobromide and the Crystalline Compound of the Present Invention The solubilities as a function of time were determined for vortioxetine hydrobromide polymorphs alpha, beta and the crystalline compound of the present invention, respectively. Therefore approximately 100 mg of each polymorph (polymorph alpha and beta were obtained according to the procedures disclosed in WO 2007/144005 A1, the crystalline compound of the present invention was obtained according to the procedure disclosed in example 1 herein) were stirred in 50 mL of a mixture of hexanol/n-heptane (1:39=v:v) at 25±1° C. Subsequently 5 mL were taken from each suspension after 1, 5, 10, 15, 30 and 60 minutes with the aid of a volumetric pipette and filtered. The concentrations of the obtained solutions were determined directly by UV-spectrophotometry (apparatus: Shimadzu UV1800) at 227 nm.

Figure 5:
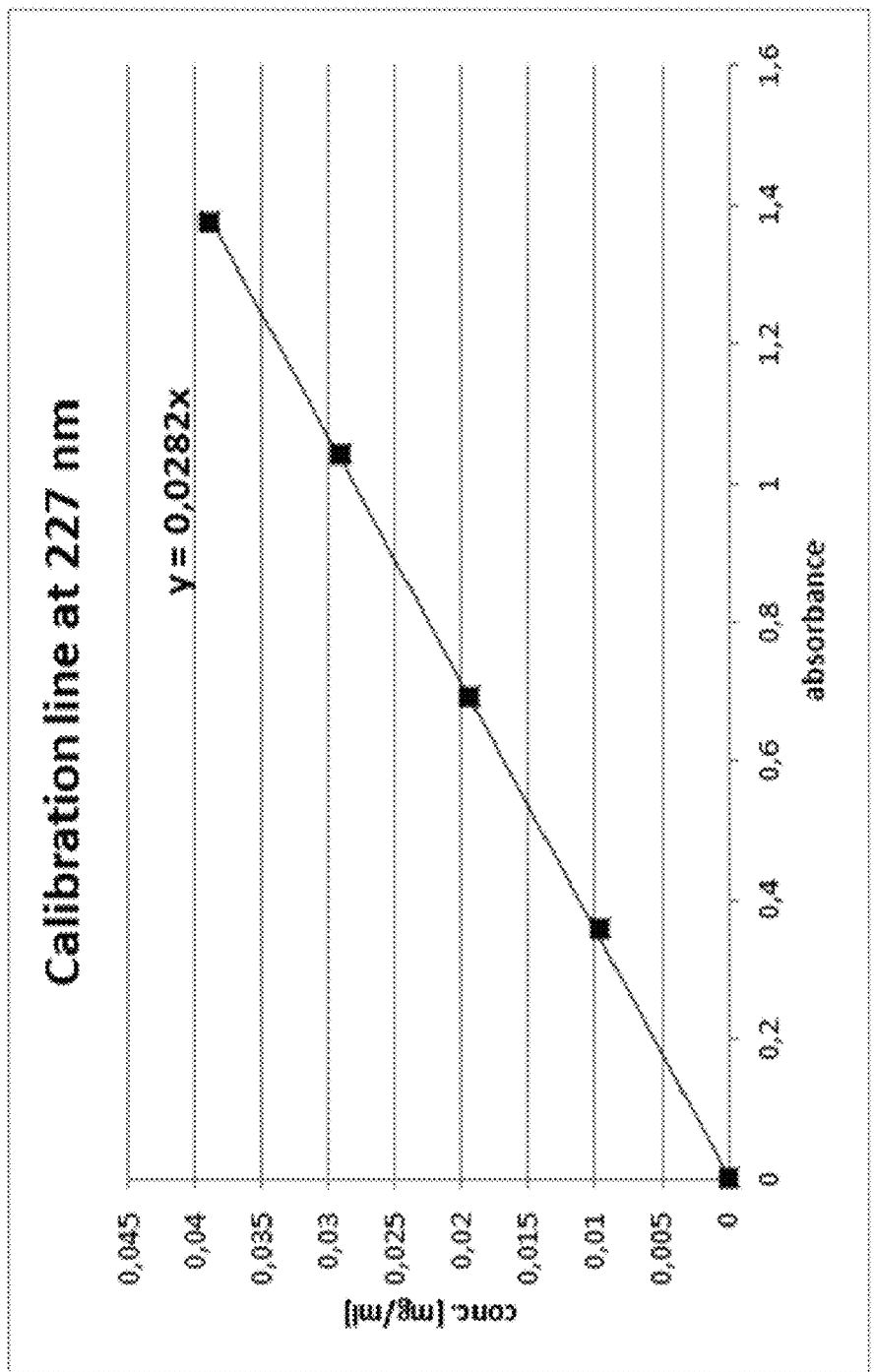
FIG. 5: Calibration line of the extinction coefficient ε=0.0282
Figure 6:
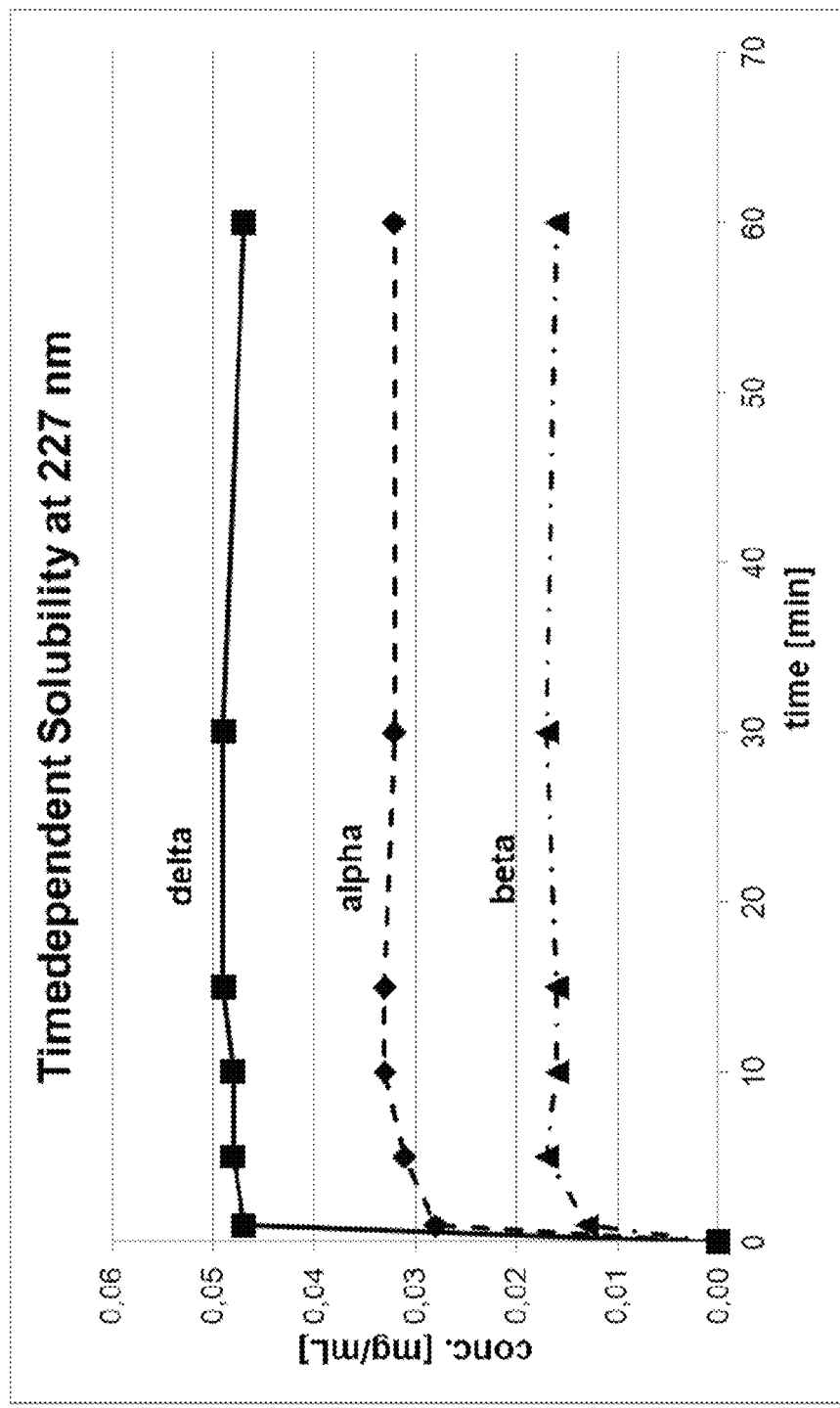
FIG. 6: Time dependent solubility curve of polymorphs alpha, beta and delta in hexanol/n-heptane (1:39=v:v) at 227 nm

The determination of the extinction coefficient was performed with polymorph delta as a calibration substance. Using 5 concentration points a calibration line was calculated by linear regression resulting in $\epsilon=0.0282$ (see FIG. 5). As can be seen from table 4 and FIG. 6 form delta shows the highest absolute solubility in hexanol/n-heptane (1:39=v:v). The relative solubilities of polymorphs alpha, beta and the crystalline compound of the present invention were calculated from the experimentally determined absolute solubility values and are displayed in table 4 as well.

TABLE 4

Absolute and relative solubilities of polymorphs alpha, beta and the crystalline compound of the present invention

| polymorph | absolute solubility in hexanol/n-heptan (1:39 = v:v) [mg/mL] | relative solubility |
| --- | --- | --- |
| alpha | 0.031 | 2.1 |
| beta | 0.015 | 1.0 |
| present invention | 0.048 | 3.2 |

Figure 7:
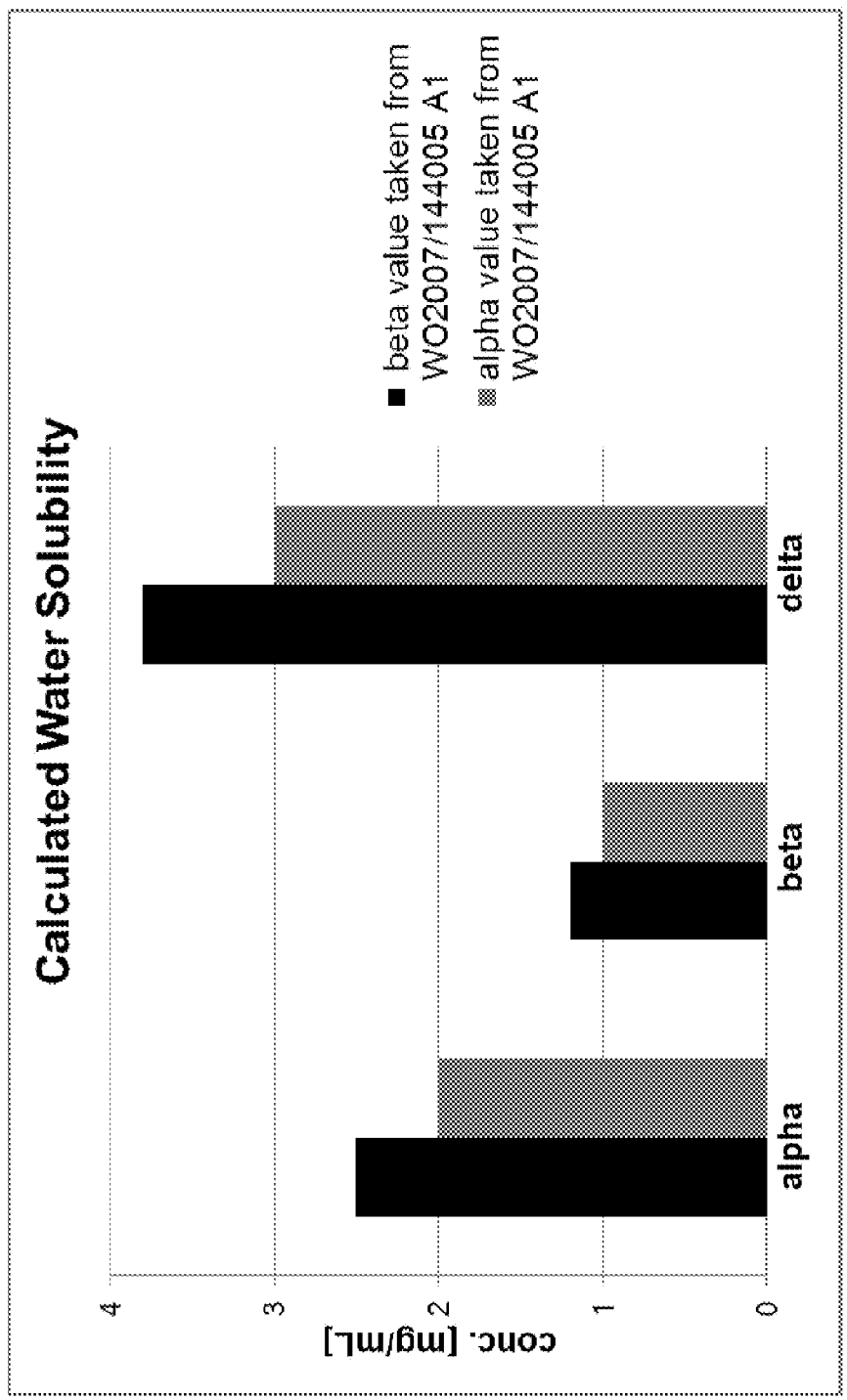
FIG. 7: Calculated water solubilities of polymorphs alpha, beta and delta
Figure 8:
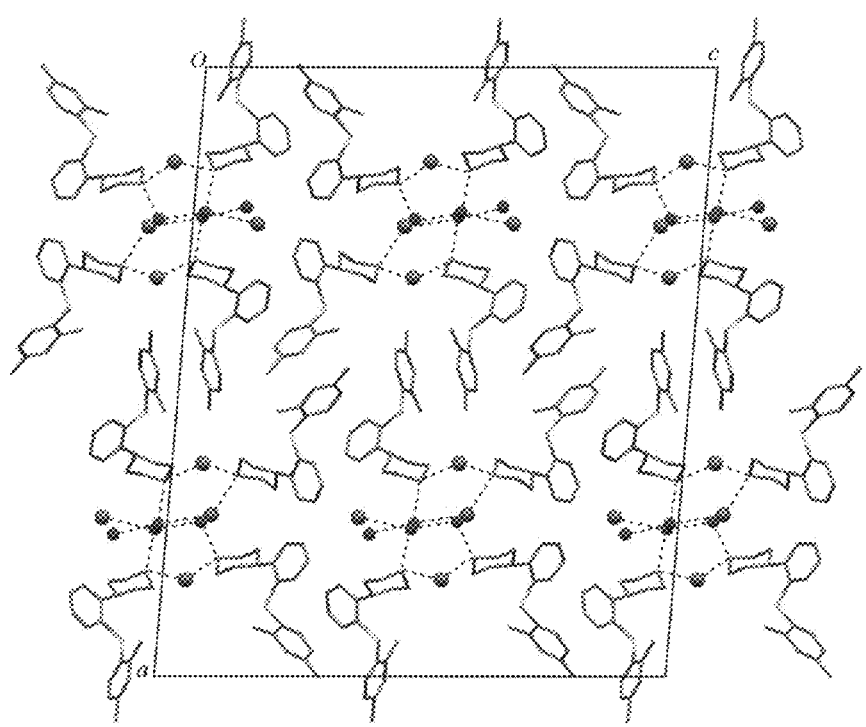
FIG. 8: Unit cell of vortioxetine hydrobromide monohydrate

Using the water solubility values of polymorphs alpha and beta provided in WO 2007/144005 A1 and the herein determined relative solubilities of polymorphs alpha, beta and delta the water solubility of the crystalline compound of the present invention can be calculated. Depending on the water solubility value used for the calculation, either the 2.0 mg/mL for polymorph alpha or the 1.2 mg/mL for polymorph beta, different water solubility values for the crystalline compound of the present invention are obtained (see table 5 and FIG. 7). However, the relative solubility remains the same in both cases and the crystalline compound of the present invention shows the highest water solubility of all three polymorphs.

TABLE 5

Calculated water solubilities of polymorphs alpha, beta and delta

| polymorph | calculated water solubility[1] [mg/mL] | calculated water solubility[2] [mg/mL] |
| --- | --- | --- |
| alpha | _2.0_ | 2.5 |
| beta | 1.0 | _1.2_ |

TABLE 5-continued

Calculated water solubilities of polymorphs alpha, beta and delta

| polymorph | calculated water solubility[1] [mg/mL] | calculated water solubility[2] [mg/mL] |
|---|---|---|
| present invention | 3.0 | 3.8 |

[1]calculation with water solubility value of polymorph alpha from WO 2007/144005 A1
[2]calculation with water solubility value for polymorph beta from WO 2007/144005 A1

The invention claimed is:

1. A crystalline compound comprising a hydrobromic acid (HBr) salt of a compound of formula I (1-{2-[(2,4-dimethylphenyl) sulfanyl]phenyl}piperazine)-{2-[(2,4-dimethylphenyl)-sulfanyl]phenyl}piperazine),

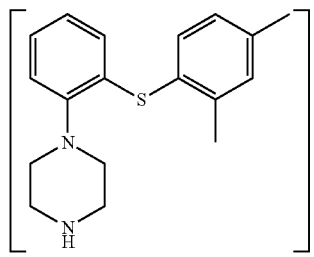

formula I having an XRPD pattern with characteristic peaks (expressed in 2θ±0.2° 2θ (CuKα radiation)) at 5.5°, 14.8°, 16.7° and 20.0°.

2. The crystalline compound of claim 1, characterized in that it has an XRPD pattern with characteristic peaks (expressed in 2θ±0.2° 2θ (CuKα radiation)) at 5.5°, 14.8°, 16.7°, 20.0°, 27.6°, 28.1°, 28.4°, 28.6°, 29.1°, 30.5° and 34.4°.

3. The crystalline compound of claim 1, characterized in that the molar ratio of the compound of formula I and the hydrobromic acid is in the range of from 1:0.8 to 1:1.2.

4. The crystalline compound according to claim 1, characterized in that it has an infrared spectrum comprising peaks at wavenumbers of 2484±2 cm$^{-1}$, 2472±2 cm$^{-1}$, 1586±2 cm$^{-1}$, 1438±2 cm$^{-1}$ and 764±2 cm$^{-1}$.

5. The crystalline compound according to claim 1, characterized in that it has a water content of less than 0.7 wt-%.

6. The crystalline compound according to claim 1, characterized in that it has an amount of residual solvents of less than 0.2 wt-%.

7. A pharmaceutical composition comprising the crystalline compound of claim 1 and at least one pharmaceutically acceptable excipient, wherein the pharmaceutical composition is in an oral dosage form.

8. A method for the treatment of major depressive disorder and/or generalized anxiety disorder comprising administering an effective amount of the pharmaceutical composition according to claim 7 to a patient suffering from major depressive disorder and/or generalized anxiety disorder.

9. A crystalline monohydrate of vortioxetine hydrobromide exhibiting monoclinic cells having space group $P2_{1/c}$ and having the parameters
a=37.33+/−0.6 Å
b=6.46+/−0.1 Å
c=31.36+/−0.5 Å
α=90°
β=94.9°+/−0.5°
γ=90°
Z=16
as determined by X-ray structural analysis; and
wherein the monohydrate has an XRPD pattern comprising characteristic peaks (expressed in 2θ±0.2° 2θ (CuKα radiation)) at 5.6°, 8.7°, and 9.4°.

10. The crystalline monohydrate of vortioxetine hydrobromide according to claim 9, wherein the molar ratio of vortioxetine hydrobromide and water is in the range from 1:0.8 to 1:1.2.

11. A method for the preparation of the crystalline monohydrate of vortioxetine hydrobromide according to claim 9 comprising the step of evaporating an aqueous alcoholic solution of vortioxetine hydrobromide at room temperature and recovering the crystals, wherein the alcohol in the aqueous alcoholic solution is selected from methanol, ethanol or mixtures thereof.

12. The method according to claim 11, wherein the concentration of the alcohol in the aqueous alcoholic solution is in the range from 50 to 96 wt-%.

13. A method for the preparation of the crystalline compound according to claim 1, comprising heating a crystalline hydrate of vortioxetine hydrobromide to a temperature ranging from 120° C. to 150° C. and recovering the crystals, where the crystalline hydrate of vortioxetine hydrobromide exhibits monoclinic cells having space group $P2_{1/c}$ and having the parameters
a=37.33+/−0.6 Å
b=6.46+/−0.1 Å
c=31.36+/−0.5 Å
α=90°
β=94.9°+/−0.5°
γ=90°
Z=16
as determined by X-ray structural analysis.

* * * * *

UNITED STATES PATENT AND TRADEMARK OFFICE
CERTIFICATE OF CORRECTION

PATENT NO. : 9,499,504 B2  
APPLICATION NO. : 14/429388  
DATED : November 22, 2016  
INVENTOR(S) : Andreas Hotter, Michael Enders and Ulrich Griesser Page 1 of 1

It is certified that error appears in the above-identified patent and that said Letters Patent is hereby corrected as shown below:

In the Claims

In Claim 1, please delete the second repetition of the phrase "1-{2-[(2,4-dimethylphenyl)sulfanyl]phenyl} piperazine" from the claim.

Signed and Sealed this  
Third Day of July, 2018

Andrei Iancu  
*Director of the United States Patent and Trademark Office*